United States Patent
Tonks

(10) Patent No.: US 9,970,044 B2
(45) Date of Patent: *May 15, 2018

(54) METHOD FOR IMPROVING MEASUREMENT ACCURACY AND DEVICES AND SYSTEMS RELATED THERETO

(71) Applicant: Abbott Diabetes Care Inc., Alameda, CA (US)

(72) Inventor: Simon Tonks, Abingdon (GB)

(73) Assignee: Abbott Diabetes Care Inc., Alameda, CA (US)

( * ) Notice: Subject to any disclaimer, the term of this patent is extended or adjusted under 35 U.S.C. 154(b) by 17 days.

This patent is subject to a terminal disclaimer.

(21) Appl. No.: 15/046,081

(22) Filed: Feb. 17, 2016

(65) Prior Publication Data

US 2016/0244800 A1    Aug. 25, 2016

Related U.S. Application Data

(63) Continuation of application No. 14/134,769, filed on Dec. 19, 2013, now Pat. No. 9,273,337.

(60) Provisional application No. 61/745,457, filed on Dec. 21, 2012.

(51) Int. Cl.

| | |
|---|---|
| *C12Q 1/00* | (2006.01) |
| *C12Q 1/26* | (2006.01) |
| *C12Q 1/32* | (2006.01) |
| *G01N 27/12* | (2006.01) |
| *G01N 27/22* | (2006.01) |
| *G01N 27/327* | (2006.01) |

(52) U.S. Cl.
CPC .............. *C12Q 1/006* (2013.01); *C12Q 1/26* (2013.01); *C12Q 1/32* (2013.01); *G01N 27/12* (2013.01); *G01N 27/226* (2013.01); *G01N 27/3272* (2013.01)

(58) Field of Classification Search
None
See application file for complete search history.

(56) References Cited

U.S. PATENT DOCUMENTS

| | | | |
|---|---|---|---|
| 5,628,890 A | 5/1997 | Carter et al. | |
| 6,071,391 A | 6/2000 | Gotoh et al. | |
| 6,143,164 A | 11/2000 | Heller et al. | |
| 6,592,745 B1 | 7/2003 | Feldman et al. | |
| 6,616,819 B1 | 9/2003 | Liamos et al. | |
| 6,736,957 B1 | 5/2004 | Forrow et al. | |
| 6,764,581 B1 | 7/2004 | Forrow et al. | |
| 6,893,545 B2 | 5/2005 | Gotoh et al. | |
| 7,311,812 B2 | 12/2007 | Forrow et al. | |
| 7,501,053 B2 | 3/2009 | Karinka et al. | |
| 7,754,093 B2 | 7/2010 | Forrow et al. | |
| 7,866,026 B1 | 1/2011 | Wang et al. | |
| 8,262,874 B2 | 9/2012 | Forrow et al. | |
| 2006/0025662 A1 | 2/2006 | Buse et al. | |
| 2006/0091006 A1 | 5/2006 | Wang et al. | |
| 2007/0068807 A1 | 3/2007 | Feldman et al. | |
| 2007/0095661 A1 | 5/2007 | Wang et al. | |
| 2007/0108048 A1 | 5/2007 | Wang et al. | |
| 2007/0199818 A1 | 8/2007 | Petyt et al. | |
| 2007/0272563 A1 | 11/2007 | Petyt et al. | |
| 2008/0066305 A1 | 3/2008 | Wang et al. | |
| 2008/0093230 A1 | 4/2008 | Diamond et al. | |
| 2008/0102441 A1 | 5/2008 | Chen et al. | |
| 2008/0148873 A1 | 6/2008 | Wang | |
| 2008/0267823 A1 | 10/2008 | Wang et al. | |
| 2009/0095625 A1 | 4/2009 | Forrow | |
| 2009/0294306 A1 | 12/2009 | Feldman et al. | |
| 2010/0206750 A1 | 8/2010 | Tonks | |
| 2012/0234700 A1 | 9/2012 | Deng | |
| 2012/0239304 A1 | 9/2012 | Heyer et al. | |
| 2012/0241318 A1 | 9/2012 | Neel et al. | |

FOREIGN PATENT DOCUMENTS

| | | |
|---|---|---|
| WO | 2008/040982 | 4/2008 |
| WO | 2008/150436 | 12/2008 |

OTHER PUBLICATIONS

Hellman (2012) "Glycemic variability in the use of point-of-care glucose meters" Diabetes Spectrum 25(3):135-140.
Teodorczyk et al. (2012) "Hematocrit compensation in electrochemical blood glucose monitoring systems" Journal of diabetes science and technology 6(3): 648-655.
Clark et al. (1987) "Evaluating Clinical Accuracy of Systems for Self-Monitoring of Blood Glucose" Diabetes Care 10(5): 622-628, filed in parent application.

*Primary Examiner* — Michelle F. Paguio Frising
(74) *Attorney, Agent, or Firm* — Vorys, Sater, Seymour and Pease LLP

(57) ABSTRACT

The present disclosure relates to methods and devices for providing accurate measurement of a property of a sample. The method comprises obtaining a plurality of independent measurements of the property. The plurality of values of the property of the sample obtained by the plurality of independent measurements is compared to determine whether one or more of the values is an outlier.

22 Claims, 7 Drawing Sheets

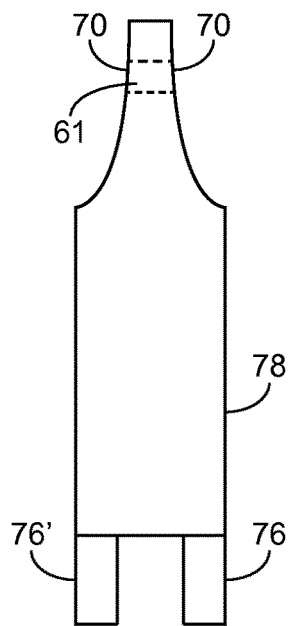
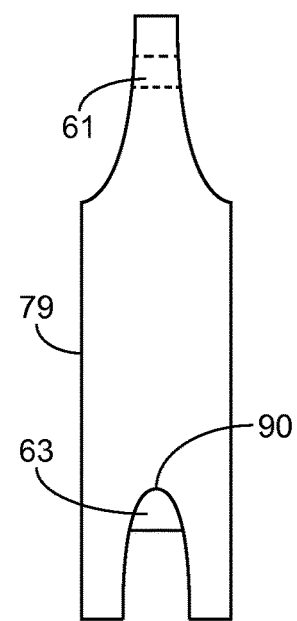
FIG. 7A  FIG. 7B
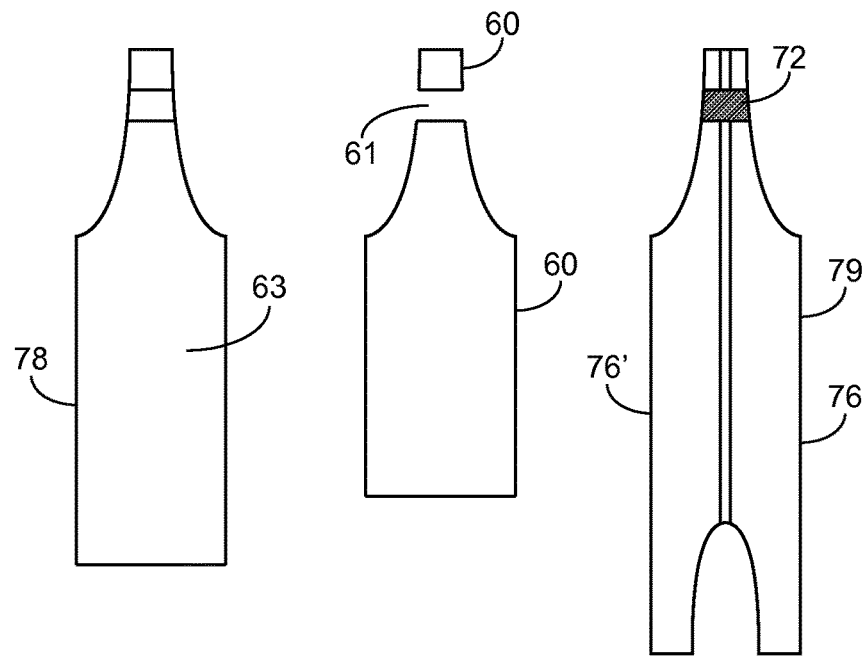
FIG. 7C

METHOD FOR IMPROVING MEASUREMENT ACCURACY AND DEVICES AND SYSTEMS RELATED THERETO

CROSS-REFERENCE TO RELATED APPLICATIONS

This application is a continuation of U.S. patent application Ser. No. 14/134,769 filed Dec. 19, 2013, now issued as U.S. Pat. No. 9,273,337, which application claims the benefit of U.S. Provisional Patent Application No. 61/745,457 filed Dec. 21, 2012, which applications are incorporated herein by reference in their entirety.

INTRODUCTION

Analyte sensors are routinely used to monitor levels of analytes of interest in body fluids of subjects. An increasing number of people and their physicians depend upon the analyte levels measured by analyte sensors to manage analyte level in the body. For example, glucose sensors are used routinely on and by patients diagnosed with diabetes to monitor the concentration of glucose in a body fluid, such as, whole blood.

The growing demand for analyte sensors for detecting and measuring analytes in body fluids has led to an increased interest in devices for quickly, and accurately measuring and monitoring analytes of interest.

SUMMARY

The present disclosure relates to methods and devices for providing accurate measurement of a property of a sample. The method comprises obtaining a plurality of independent measurements of the property. The plurality of values of the property of the sample obtained by the plurality of independent measurements is compared to determine whether one or more of the values is an outlier. The values may be compared to each other, or to a reference value, or to an average value.

Embodiments of the present disclosure relate to a method for measuring a property of a sample. The method may include obtaining at least three independent measurements of the property of the sample, comparing the results of the three or more independent measurements to determine whether there is an outlier(s). In certain cases, the method may further include excluding any outlier(s) from the calculation of a single value of the property of the sample. In certain embodiments, the three or more independent measurements of the property of the sample may be obtained by using a single sensor.

In certain embodiments, the method may include obtaining a first measurement of the property of the sample; obtaining a second measurement of the property of the sample; obtaining a third measurement of the property of the sample; deriving a first value, a second value and a third value of the property using the first, second, and third measurements, respectively; comparing the first, second, and third values to determine whether one of the values is an outlier.

In certain cases, the method may further include providing a single value of the property based on the values that are in agreement while excluding the outlier(s), if any.

In certain cases, the method includes obtaining a single value from the first, second, and third values when the first, second, and third values are in agreement and no outlier is detected.

In certain cases, the method may include obtaining more than three measurements of the property of the sample and the method may further include deriving the more than three values; comparing the more than three values; determining the presence of an outlier and providing a single value of the property based on the values that are in agreement while excluding any outlier(s). In certain cases, the more than three measurements may be four, five, six, or more measurements. Accordingly, in certain cases, the method may include obtaining four or more measurements of the property of the sample and the method may further include deriving four or more values; comparing the four or more values; determining the presence of an outlier and providing a single value of the property based on the values that are in agreement while excluding any outlier(s).

In certain embodiments, the method may further include reporting an error when none of the values determined from a plurality of measurements are in agreement.

In certain embodiments, the method further includes selecting the most reliable of the three or more values measured as the measurement value of the property, when none of the values are in agreement. The most reliable value may be selected based on prior measurements, for example.

In certain embodiments, the property of a sample being measured may be hematocrit, concentration of an analyte, viscosity, temperature, or oxygenation. In certain embodiments, the analyte may be oxygen, uric acid, ascorbic acid, Acetaminophen, maltose, glucose, acetyl choline, amylase, bilirubin, cholesterol, chorionic gonadotropin, hemoglobin, glycosylated hemoglobin (HbAlc), creatine kinase (e.g., CK-MB), creatine, DNA, fructosamine, glucose, glutamine, growth hormones, hormones, ketones, ketone bodies, lactate, peroxide, prostate-specific antigen, prothrombin, RNA, thyroid stimulating hormone, or troponin.

In certain embodiments, the method may include measuring a property of the sample and level of an analyte in the sample, wherein the measuring the property includes obtaining at least three measurements of the property of the sample, for example, obtaining a first measurement of the property of the sample; obtaining a second measurement of the property of the sample; obtaining a third measurement of the property of the sample; deriving a first value, a second value and a third value of the property using the first, second, and third measurements, respectively; comparing the first, second, and third values to determine whether one of the values is an outlier. In certain embodiments, the method may further include measuring a level of an analyte in the sample. In this embodiment, the property of the sample may be hematocrit, viscosity, temperature and the analyte may be oxygen, uric acid, ascorbic acid, Acetaminophen, maltose, glucose, acetyl choline, amylase, bilirubin, cholesterol, chorionic gonadotropin, hemoglobin, glycosylated hemoglobin (HbAlc), creatine kinase (e.g., CK-MB), creatine, DNA, fructosamine, glucose, glutamine, growth hormones, hormones, ketones, ketone bodies, lactate, peroxide, prostate-specific antigen, prothrombin, RNA, thyroid stimulating hormone, or troponin. Accordingly, the method may include measuring a property of the sample as set forth above and level of an analyte in the sample as set forth above, where the property and analyte may be any combination of the properties and analytes set forth above, e.g., the property may be hematocrit and the analyte may be glucose; the property may be hematocrit and the analyte may be glucose; the property may be hematocrit and the analyte may be glucose; the property may be hematocrit and the analyte may be lactate; the property may be hematocrit and the analyte may be ketone or ketone bodies; the property may be hematocrit and the analyte may be cholesterol; the property may be viscosity and the analyte may be glucose; the property may be viscosity and the analyte may be lactate; the property may be viscosity and the analyte may be ketone or ketone bodies; the property may be viscosity and the analyte may be cholesterol; the property may be temperature and the analyte may be glucose; the property may be temperature and the analyte may be lactate; the property may be temperature and the analyte may be ketone or ketone bodies; the property may be temperature and the analyte may be cholesterol; and the like.

In certain embodiments, the method may further include determining that at least two of the values of the property of the sample are in agreement and using the values that in agreement to obtain a single value and using the single value to determine the concentration of the analyte, wherein the concentration of the analyte is determined using both the analyte measurement and the measurements of the property, wherein the concentration of the analyte determined using the measurements of the property of the sample has a higher accuracy than a concentration of the analyte determined without the use of the measurements of the property of the sample.

In certain embodiments, the method may further include determining that at least two of the values of the property of the sample are in agreement and using the values that in agreement to determine two concentrations of the analyte and determining a concentration of the analyte from the two concentrations, wherein the concentration of the analyte is determined using both the analyte measurement and the measurements of the property, wherein the concentration of the analyte determined using the measurements of the property of the sample has a higher accuracy than a concentration of the analyte determined without the use of the measurements of the property of the sample.

In certain embodiments, the method may further include determining that none of the values of the property of the sample are in agreement. The method may then further include determining the concentration of the analyte without using the measurement of the property of the sample.

In certain cases, the determining of at least three, or more, values of the property of the sample, may be performed using the same sensor.

In certain cases, the method may include obtaining the plurality of measurements of the property of the sample by using a biosensor that has been contacted with the sample. In certain cases, the biosensor may include a plurality of electrodes for obtaining the plurality of measurements.

In certain cases, the method may include obtaining the first, second, and third measurements by using a biosensor that has been contacted with the sample. In certain cases, the biosensor may include a first electrode, a second electrode, and a third electrode, which may be used for obtaining the first, second, and third measurements.

In certain embodiments, the property of the sample being measured is hematocrit and obtaining a plurality of measurements of the hematocrit of the sample may include measuring a hematocrit related signal using a biosensor that includes a plurality of electrodes.

In certain embodiments, the hematocrit of the sample is measured by using a biosensor that includes at least three electrodes. In certain cases, the biosensor may include a first, second and third electrode.

In certain embodiments, the first measurement of hematocrit of the sample may include determining fill-time of the sample, or a velocity of movement of sample in a sample chamber of the biosensor, or viscosity of the sample.

In certain cases, the first measurement may include determining fill-time of the sample. In certain embodiments, the fill-time may be determined by measuring time elapsed between detecting a signal between the first electrode and the second electrode, when the sample completes a circuit between the first electrode and the second electrode and another signal between the first electrode and the third electrode and/or between the second electrode and the third electrode, when the sample completes a circuit between the first and the third electrode and/or the second and the third electrode; obtaining the second measurement may include measuring a first signal at one of the three electrodes after the sample chamber is substantially filled with the sample; and obtaining the third measurement may include measuring a second signal at one of the three electrodes, wherein the first and second signals are measured at different electrodes.

In certain cases, the sensor includes an enzyme responsive to an analyte and a redox mediator, the method further includes measuring an analyte related signal at the second electrode after measuring the first signal and determining concentration of the analyte using the analyte related signal.

In certain embodiments, the first and second signals are selected from the group consisting of voltage, current, resistance, capacitance, charge, conductivity, or combination thereof. In certain embodiments, the first and second signals are current. In certain embodiments, the first signal is measured at the second electrode and the second signal is current measured at the third electrode, where the first and second signals are current.

In certain embodiments, determining concentration of the analyte using the analyte related signal includes correcting the analyte related signal using a value of the property of the sample, wherein the property is the concentration of an interferent that may produce an error or variation in measurement of analyte concentration. In certain cases, the analyte may be glucose or ketone bodies and the interferent may be hematocrit, acetaminophen, uric acid, or ascorbic acid. Accordingly, in certain embodiments, a method for determining the concentration of an analyte in a sample is provided, where the method includes measuring an analyte related signal and obtaining at least three measurements of an interferent present in the sample, which interferent may produce an error or variation in measurement of the analyte concentration; deriving three values of concentration of the interferent; determining a single value for concentration of the interferent based on at least two values that are in agreement; using the single value of concentration of the interferent to correct the analyte related signal and to determine a corrected analyte concentration, where the corrected analyte concentration is more accurate than the analyte concentration that has not been corrected using the single value of concentration of the interferent. In certain cases, two or more interferents may be measured in at least three independent measurements and measurements of the interferents may be used to correct the analyte related signal or the analyte concentration obtained from the analyte related signal.

In certain embodiments, the analyte may be glucose and the enzyme present in the sample chamber of the sensor may be glucose dehydrogenase or glucose oxidase. In some examples, the glucose dehydrogenase may be nicotinamide dinucleotide glucose dehydrogenase (NAD-GDH), pyrrole quinoline quinone glucose dehydrogenase (PQQ-GDH) or flavin-adenine dinucleotide glucose dehydrogenase (FAD-GDH). In other examples, the analyte may be beta-hydroxybutyrate (ketone) and the enzyme may be hydroxybutyrate dehydrogenase. As used herein, the terms, "sensor", "biosensor", and "electrochemical sensor" are used interchangeably.

In certain embodiments, the first, second, and third electrodes are coplanar. In certain embodiments, one of the first, second, and third electrodes is in facing configuration with the other two electrodes.

In certain embodiments, the electrodes are arranged such that the sample contacts the first electrode before contacting the second electrode and contacts the second electrode before contacting the third electrode.

In other embodiments, the electrodes are arranged such that the sample contacts the first and second electrodes simultaneously and before contacting the third electrode.

An aspect of the present invention relate to a method for using an analyte sensor, the method may include obtaining first, second, and third measurements of a property of a sample applied to a sensor that includes a sample chamber that includes a first electrode, a second electrode, and a third electrode; an enzyme responsive to the analyte and a redox mediator. In certain cases, the obtaining the first measurement may include determining fill-time by measuring time elapsed between detecting a signal between the first electrode and the second electrode and another signal between the first electrode and the third electrode and/or between the second electrode and third electrode. In certain cases, the property of the sample being measured may be hematocrit. The fill-time measurement may be related to the hematocrit of the sample. In certain embodiments, obtaining the second measurement of hematocrit may include measuring a first signal at the second electrode after the sample chamber is substantially filled with the sample, wherein the first signal is related to hematocrit of the sample. In certain embodiments, obtaining the third measurement of hematocrit may include measuring a second signal at the third electrode after measuring the analyte related signal, wherein the second signal is related to hematocrit of the sample. In certain embodiments, the method may include measuring the level of an analyte in the sample. In certain cases, the method may include measuring an analyte related signal at the second electrode after measuring the first signal; and determining concentration of the analyte. In certain cases, the first signal measured at the second electrode, after the sample chamber is substantially filled with the sample, is substantially independent of the analyte concentration. Accordingly, the method includes obtaining at least three independent measurements of the hematocrit of the sample, which measurements may then be used to determine hematocrit with a higher accuracy than that determined using only a single measurement. Further, since each hematocrit measurement is made in different manner, rather than obtaining hematocrit of the sample by three readings using the same method, this method offers additional advantages, such as, ability to weigh the different measures differently. For example, a measurement obtained by a method known to be less prone to errors or variation may be weighted higher than the measurement obtained by another method which is known to have some variability.

In certain cases, the method may include deriving first, second, and third hematocrit values of the sample using the fill-time, the first signal, and the second signal. In certain cases, the method further comprises comparing the first, second, and third hematocrit values of the sample.

In certain aspects, the method may include calculating a single hematocrit value based on the first, second and third hematocrit values when the first, second, and third hematocrit values of the sample are in agreement.

In certain embodiments, the method may include calculating a single hematocrit value based on two of the first, second, and third hematocrit values when only the two of the first, second, and third hematocrit values are in agreement.

In certain cases, the method further includes correcting the concentration of the analyte according to the single hematocrit value. In certain cases, the method may include determining the concentration of the analyte where the concentration of the analyte is not corrected according to a hematocrit value, when the hematocrit values are not in agreement.

In certain examples, the first and second signals are selected from the group consisting of voltage, current, resistance, capacitance, charge, conductivity, or combination thereof.

In a further aspect of the method of determining analyte concentration, the analyte may be glucose and the enzyme may be glucose dehydrogenase or glucose oxidase. In certain cases, glucose dehydrogenase may be pyrrole quinoline quinone glucose dehydrogenase (PQQ-GDH), NAD-GDH, or flavin-adenine dinucleotide glucose dehydrogenase (FAD-GDH).

In a further aspect of the method of determining analyte concentration, the analyte may be β-hyroxybutyrate and the enzyme may be hydroxybutyrate dehydrogenase.

In certain cases, the first, second, and third electrodes of the sensor used to carry out the method of determining analyte concentration may be coplanar. In another aspect, one of the first, second, and third electrodes may be in facing configuration with the other two electrodes. In certain cases, the electrodes are arranged such that the sample contacts the first electrode before contacting the second electrode and contacts the second electrode before contacting the third electrode. In other cases, the electrodes are arranged such that the sample contacts the first and second electrodes simultaneously before contacting the third electrode.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

FIGS. 7A-7C shows an embodiment of an analyte sensor for use in the methods disclosed herein.

DETAILED DESCRIPTION OF THE INVENTION

Figure 1A:
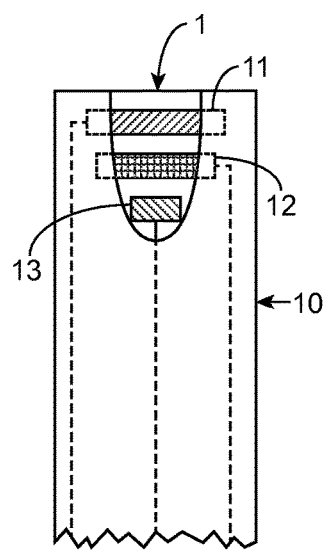
FIGS. 1A and 1B depict alternative embodiments of an analyte sensor.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be embodied by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference in their entirety to disclose and describe the methods, devices, and systems, and/or other materials. The present disclosure is controlling to the extent there is a contradiction between the present disclosure and a publication incorporated by reference.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given property described herein, any of the possible candidates or alternatives listed for that property, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

Method for Improving Measurement Accuracy

Aspects of the present disclosure relate to a method for improving measurement accuracy of a property of the sample. In general the method involves obtaining three or more independent measurements of the property of the sample and comparing the independent measurements to determine if the measurements are in agreement. In certain cases, one of the measurements may be identified as an outlier when compared to the other measurements. Accordingly, the other measurements that are in agreement with each other may be used to measure the property of the sample while excluding the outlier. As such, the property of the sample may be determined accurately. In general, combining two or more similar values of the property of the sample while excluding any outlier(s) results in an improved measurement where the measurement quality is improved by decreasing the noise for the property and increasing the signal to noise ratio for the property.

When all independent measurements of the property of the sample are in agreement, all measurements may be used to derive a single measurement of the property of the sample. As such, the property of the sample may be determined accurately.

As used herein, independent measurements of a property of the sample refers to measurements performed using different methods-rather than performing a plurality of the same measurement. Different methods for measuring a property of the sample are described in detail below.

In certain cases, the independent measurements may provide measurements of the property which measurements are not directly comparable and need a deriving step to convert the measurement into a value of the property, e.g., concentration of the property, which may then be compared to determine an accurate measurement of the property. For example, as described in the detail herein, the property may be hematocrit which may be measured by independent methods which yield hematocrit measurements that are derived to yield hematocrit values, which may then be compared to determine whether the hematocrit values are in agreement.

In certain cases, the property being measured may be concentration of an analyte, such as, glucose and a plurality of independent measurements of the concentration of the analyte may be performed. In certain cases, three independent measurements may be performed by using three different enzyme systems for measuring the analyte. For example, the analyte may be glucose and the first measurement of level of glucose in the sample may be performed using glucose oxidase to generate a first signal related to the level of glucose in a sample; the second measurement of level of glucose in the sample may be performed using pyrroloquinoline quinone (PQQ) dependent glucose dehydrogenase to generate a second signal related to the level of glucose in a sample; and the third measurement of level of glucose in the sample may be performed using flavine adenine dinucleotide (FAD) dependent glucose dehydrogenase to generate a third signal related to the level of glucose in a sample. The three signals may then be used to derive a first, a second, and a third concentration of glucose. The three concentrations of glucose may then be compared to identify an outlier. If all three concentrations are similar, then all three may be used to calculate a single concentration of glucose in the sample. If one of the concentrations is an outlier, then the other two concentrations may be used to calculate a single concentration of glucose in the sample.

In certain cases, the property of the sample may be hematocrit and the method may include determining hematocrit of the sample. As used herein, hematocrit refers to volume percentage of red blood cells in blood. Hematocrit may also be referred to as packed cell volume or erythrocyte volume fraction. The hematocrit of a sample may be measured by three independent methods. For example, a first measurement of hematocrit in the sample may be performed by measuring viscosity of the sample; a second measurement of hematocrit in the sample may be performed by measuring a potential drop across the sample; and a third measurement of hematocrit in the sample may be performed by measuring level of hemoglobin in the sample. The first, second and third measurements may then be used to determine a first hematocrit, a second hematocrit, and a third hematocrit, respectively, of the sample. The three hematocrit values may then be compared to determine if there is an outlier. If one of the three hematocrit values is an outlier, then a single hematocrit value may be determined based on the other two hematocrit values. If all three hematocrit values are in agreement, a single hematocrit value may be determined based on the three hematocrit values.

As used herein, determining a single value from two or more values can involve averaging the values. The average value may be a simple average obtained by adding the values and dividing by the number of values or the average value may be a weighted average, where one of the values is weighted more heavily than other values when calculating the average value. In certain cases, the values to be weighted more heavily may be selected based on preset lower and higher limits of hematocrit. For example, when one of the hematocrit measurements is lower than a low threshold of hematocrit, that low hematocrit measurement may be weighted less heavily or in some examples, not included in the calculations. In other cases, determining a single value from three or more values can involve calculating a median value for the three or more values. In other embodiments, the more reliable signal may be weighted more heavily. For example, one of the signals may be more reliable than the others as it is obtained by a measurement that has a greater precision than the measurements used to obtain the other signals.

As used herein, values or levels or concentrations are in agreement or are considered similar when they differ from each other by less than 20%, or less than 10%, or less than 5%, or less than 1%, or less than 0.5%, or less.

As used herein, the term "outlier" as used in context of a value of a property of a sample, refers to a value (e.g., level or concentration) that is significantly different from i) other two (or more) values (e.g., levels or concentrations for the property of the sample that were obtained by a different method); ii) an average value obtained from averaging of the values of the property of the sample obtained by the different measurement methods; iii) a reference value, the reference value may be a value obtained through characterization work or a consensus value of the property of the sample. As used herein, the phrase "significantly different" refers to a difference of 20% or more, such as a value that is different from another value by more than 20%, such as, more than 25%, or more than 30%, or more than 35%, or more than 40%, or more than 45%, or more than 50%, or more than 55%, or more than 60%, or more. Any method accepted in the art for identifying an outlier may be used in the methods described herein. As such, an outlier(s) may be identified using Dixon's Q Test, Grubbs Test, another suitable outlier testes, and/or calculating difference from a median value. Absence of detection of an outlier(s) indicates that the values are in agreement.

In certain embodiments, the method may include determining the hematocrit of a sample by using a test strip. The method for determining hematocrit of a sample by using a test strip includes contacting the sample with test strip that includes a first electrode, a second electrode, and a third electrode. After the contacting, obtaining a first measurement by determining fill-time of the sample by measuring time elapsed between detecting a signal between the first electrode and the second electrode and another signal between the first electrode and the third electrode, wherein the fill-time is related to hematocrit of the sample; obtaining the second measurement by measuring a first signal at the second electrode after the sample chamber is substantially filled with the sample, wherein the first signal is related to hematocrit of the sample; and obtaining the third measurement by measuring a second signal at the third electrode, wherein the second signal is related to hematocrit of the sample. In certain embodiments, the first, second, and third electrodes may be in the order in which the sample, filling the sample chamber, contacts the electrodes. In certain embodiments, the electrodes are arranged in a sample chamber of the test strip such that the sample contacts the first electrode before contacting the second electrode and contacts the second electrode before contacting the third electrode, where the electrodes may be arranged on the same surface of a substrate of the test strip or one of the electrodes may be in a facing configuration with the other two electrodes. In certain embodiments, the electrodes are arranged in a sample chamber of the test strip such that the sample contacts the first and second electrodes before contacting the third electrode.

In certain embodiments, the method includes using the fill-time, the first signal, and the second signal to obtain first, second, and third hematocrit values of the sample. The three hematocrit values may be compared to determine if there is an outlier. If an outlier is present, then the other two hematocrit values may be used to determine a hematocrit of the sample. If all three hematocrit values are similar, then the three values may be used to determine a hematocrit of the sample.

In certain cases, the method of determining hematocrit may include measuring an analyte related signal for which hematocrit is an interference, at two points in time, where the degree of interference is time variant. The hematocrit may be determined by using the sensitivity to hematocrit at the two different time points of measurement and having calibrations for the analyte at these two measurements. Therefore, a fourth measurement of hematocrit of a sample may be obtained and used to determine a single, more accurate level of hematocrit by using the four independently measured hematocrit values.

In other aspects of the invention, a method for using an analyte sensor is provided, the method includes contacting a sample comprising an analyte with an analyte sensor that includes a sample chamber that includes a reference/counter electrode, a working electrode, and trigger electrode; an enzyme responsive to the analyte and a redox mediator; determining fill-time of the sample by measuring time elapsed between detecting a signal between the reference/counter electrode and the working electrode and another signal between the reference/counter electrode and the trigger electrode or between the working electrode and the trigger electrode, wherein the fill-time is related to hematocrit of the sample; measuring a first signal at the working electrode after the sample chamber is substantially filled with the sample, wherein the first signal is substantially independent of the analyte concentration and is related to hematocrit of the sample; measuring an analyte related signal at the working electrode after measuring the first signal; measuring a second signal at the trigger electrode after measuring the analyte related signal, wherein the second signal is related to hematocrit of the sample; and determining concentration of the analyte.

In certain embodiments, the method includes using the fill-time, the first signal, and the second signal to obtain a first, second, and third hematocrit values of the sample.

The method may further include using two or three of the first, second, and third hematocrit values to obtain a single hematocrit value for the sample. In certain cases, whether two or three of the hematocrit values are used to obtain a single hematocrit value depends on whether one of the hematocrit values is identified as an outlier. If one of the values is identified as an outlier upon comparison to the other two values or a reference value, or an average value, then the other two values are used to determine a single value. If all three values are in agreement, then all three are used to determine a single value.

In certain embodiments, the determining of concentration of the analyte includes correcting the concentration of the analyte according to the single hematocrit value. In certain embodiments, when none of the hematocrit values are in agreement and a single hematocrit value cannot be determined, the determining of concentration of the analyte does not include correcting the concentration of the analyte.

In certain embodiments, the surface area of the first, second, and third electrodes is clearly defined. As such, in certain embodiments, the sensors generally have first, second, and third electrodes with a set surface area that is kept constant between different sensors.

In certain embodiments, the first signal related to hematocrit as measured at the second electrode, such as a working electrode, may be influenced by the surface area of the electrode. In certain embodiments, the second signal related to hematocrit as measured at the third electrode, such as a trigger electrode, may be influenced by the surface area of the electrode. Therefore, the surface area of the second and third electrodes may be kept constant between different sensors being used in the method of measuring hematocrit.

In other embodiments, the surface area of the electrodes may not be kept constant but the surface area is known and used to normalize the signal measured to the signal that would be measured from a set surface area.

In certain cases, none of the hematocrit values may be in agreement. In such a scenario, the analyte concentration may not be adjusted or the user may be prompted to repeat the test using another test strip. In this embodiment, determining the concentration of the analyte does not include correcting the analyte concentration using the hematocrit value.

The terms, "sensor", "biosensor", or "test strip", are used interchangeably.

In certain cases, the method may involve inserting the sensor in a meter, wherein insertion of the sensor results in the meter being turned on. The sensor may include a first, second and a third electrode as illustrated in FIGS. 1A and 1B, 2, and 6-8. For example, as shown in the sensor 10 of FIG. 1A, the first electrode 11 may be closest to the sample application site 1, followed by the second electrode 12, and third electrode 13. The sensor in FIG. 1A is depicted as having a first substrate onto which the electrodes are disposed and further having an insulative layer, with a cut-out for the sample chamber, disposed on the electrodes, the cut-out exposes the electrodes in the sample chamber while covering other portions of the electrodes. Accordingly, within the sample chamber, the electrodes are disposed such that a sample applied at the tip of the sensor at application site 1, contacts the first electrode 11 first, then the second electrode 12, and then the third electrode 13. The conductive trace portions of the electrodes which connect the electrodes to a meter are covered by the insulative layer. These sensors may have an additional layer, such as a second substrate disposed over the insulative layer. The cut out in the insulative layer and the first and second substrates defining the sample chamber.

In other embodiments, the first electrode may be on a first substrate of the sensor while the second and/or the third electrode may be on a second substrate of the sensor, where the arrangement of the electrode with regard to the sample application site may be as described above.

Figure 1B:
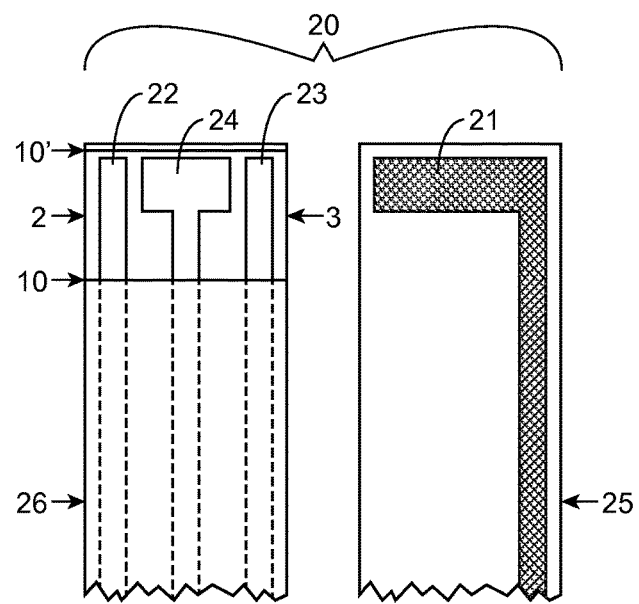

In other embodiments, the sensor may be as shown in FIG. 1B. In FIG. 1B, the sensor 20 includes a first electrode 21 on a first substrate 25; second electrode 22 and 23, and third electrode 24 on a second substrate 26. In the assembled sensor, the first electrode is a facing orientation to electrodes 22, 23, and 24. In the sensor of FIG. 1B, the sample may be filled from either side entrance 2 or 3. A spacer layer 10 and 10' in combination with the two substrates 25 and 26 define the sample chamber. The sensor in FIG. 1B includes two side entrances 2 and 3 either of which can be used to fill the sensor with a sample. In these embodiments, the sample may contact the first (21) and second (22) electrodes simultaneously and before the sample contacts the third electrode 24, when the sample enters at entrance 2. In other embodiments, the sample enters at entrance 3 and contacts electrodes 21 and 23 simultaneously before contacting electrode 22.

Following insertion of the sensor and the waking up of the meter, a sample may be applied to the sensor at the sample application site. The presence of the sample in the sample chamber may be determined by detecting a signal between the first and the second electrode. The substantial filling of the sample chamber by the sample may be determined by detecting a signal between the first electrode and the third electrode. For example, the presence of the sample in the sample chamber of sensor 10 may be determined by detecting a signal between the first (11) and at the second (12) electrode. The substantial filling of the sample chamber by the sample may be determined by detecting a signal between the first electrode 11 and the third electrode 13 or second electrode 12 and third electrode 13. The time difference between detecting the signal between the first and at the second electrode and detecting a signal between the first electrode and the third electrode or the second electrode and the third electrode may be used to determine fill time of sample. In general, the fill time of the sample is related to the sample viscosity which in turn is related to sample hematocrit, the higher the hematocrit, the greater the fill time. In certain embodiments, a signal may be applied between the first and second electrodes throughout the time between waking up the meter and detection of a response at the second electrode and a signal may be applied between the first and third electrodes throughout the time between waking up the meter and detection of a response at the third electrode. In other embodiments, a signal may be applied between the first and second electrodes throughout the time between waking up the meter and detection of a response at the second electrode and a signal may be applied between the first and third electrodes after detection of a response at the second electrode. In certain cases, the signal applied between the first and second electrodes may be terminated after a response is detected at the second electrode.

In certain cases, the fill time may be compared to a specified fill time range, to determine if the fill time is within the specified range. If the fill time is within the specified range, then the assay may proceed to the next step. If the fill time is lower or higher than the specified range, an error signal may be generated. The user may then be prompted to repeat the sample application step, using the same strip or a different strip. The specified range for the fill time may depend on the test strip used, the volume of the sample, or the ambient temperature. In certain embodiments, the specified range for fill time may be 0.2 to 5 seconds (sec), for example, 0.3 to 4 sec, or 0.5 to 3 sec, or 0.5 to 1 sec.

Detection of substantial filling of the sample chamber by the sample may be followed by measuring a first response at the second electrode. This response may be substantially dependent upon the hematocrit of the sample. This response may be determined after applying a signal between the first and second electrodes. The signal applied to the first and second electrodes may be similar to the signal applied to first and second electrodes while filling of the sample chamber with the sample or it might be higher or lower than the signal applied to first and second electrodes while filling of the sample chamber. In certain cases, the first and second electrodes may be disconnected after the sample chamber has been filled and then reconnected to apply a signal between the first and second electrodes.

The first response measured at the second electrode may be measured by making measurements at a high sampling frequency immediately after filling of the sample chamber or reapplication of signal to the first and second electrodes. At this time, i.e., at less than 0.1 sec, or less than 0.05, or less than 0.025, or less than 0.01, or less than 1 millisecond, or less than 1 microsecond, or less after filling of the sample chamber or application of signal between first and second electrodes after the sample chamber has been determined to be substantially filled by the sample, the signal at the second electrode is largely related to sample hematocrit. In certain cases, the signal measured at the second electrode may be an average of two or more signals measured at the second electrode, for example, the signal may be an average of three signals measured over a sampling window of 60 microseconds, or 50 microseconds, or 40 microseconds, or 30 microseconds, or 20 microseconds, or 10 microseconds.

The signal measured at the second electrode is related to the hematocrit of the sample. In general, the lower signal, the higher the hematocrit. In certain cases, the signal measured at the second electrode may be current. In certain cases, the current may be charging current. The charging current may be largely a non-Faradaic charging current. A largely non-Faradaic current may include a minor Faradic component.

Following measurement of a response at the second electrode, a signal may be applied between the first and third electrode and a response measured at the third electrode. In general, this response is related to the hematocrit of the sample. In general, the higher the hematocrit, the lower the signal measured at the third electrode. In certain cases, the response may be the current measured at the third electrode due to attenuated diffusion rates and/or a potential drop such that the voltage applied at the electrode is lowered.

In certain cases, the method of determining hematocrit may include measuring analyte related signal, for example, glucose related signal, at two different time points after contacting the sample with test strip. A first analyte concentration determination as measured at a first time differs from a second analyte concentration measured at a second time based on hematocrit due to a difference in sensitivity to hematocrit at the two different measurement times. The difference in the first and second analyte related signals may be used to calculate the hematocrit. Therefore, a fourth measurement of hematocrit of a sample may be obtained and used to determine a single, more accurate level of hematocrit by using the four independently measured hematocrit values.

The fill time, the first response, the second response, and the analyte signal integrated at two time points provide four independent measures of the sample hematocrit. These three or four independent measures may then be used to derive three or four independently measured hematocrit values of the sample The three or four independently measured hematocrit values of the sample may be compared to determine whether an outlier(s) is present. The values that are in agreement may be combined to yield a single value while excluding any outliers.

In certain cases, the sample chamber may include reagents for detecting the level of an analyte of interest present in the sample chamber. For example, an enzyme that reacts with the analyte to generate an analyte concentration dependent signal may be present in the sample chamber, for example, disposed on the second electrode. In these cases, an analyte dependent response may be measured at one of the electrodes, for example, the second electrode. The analyte dependent response may be used to determine the analyte concentration.

In certain cases, the signal applied to the electrodes may be voltage or current. In certain embodiments, the signal or response detected at an electrode may be voltage, current, resistance, or conductivity.

In certain cases, the values derived from the three or more measurement may not be in agreement with each other. In such a case, the method may further comprise, indicating an error or not adjusting the analyte concentration based on the hematocrit related values.

In certain cases, the method may also include measuring the ambient temperature. In certain cases, the ambient temperature may be within a specific limit. If the ambient temperature is within the specified limit, then temperature compensation is used while calculating the property of a sample and/or the concentration of an analyte in the sample. In certain cases, the ambient temperature may be outside of the specified temperature limit. If the ambient temperature is outside the specified temperature limit, an error is reported. In certain cases, the ambient temperature may be measured by a measuring device into which the test strip is inserted by means of a temperature measurement instrument, such as, a thermometer, a thermistor, a pyrometer, a thermocouple, and the like. The temperature may be measured before applying a sample to the test strip. In certain cases, the temperature may be measured after applying a sample to the test strip. In certain embodiments, the property of the sample may be hematocrit. In certain cases, the analyte may be glucose. In certain cases, the temperature compensation may include applying an algorithm to the measured value for the property and an analyte. In certain cases, the algorithm may include a temperature compensation factor that may be used to calculate a temperature compensated value. The temperature compensation factor may be a predetermined number.

Substrates and/or insulative layer or spacer layer of the sensors used in the methods disclosed herein may be made of a flexible polymer, such as a polyester (e.g., Mylar™ and polyethylene terephthalate (PET)), polyethylene, polycarbonate, polypropylene, nylon, polyvinyl chloride (PVC), polyurethanes, polyethers, polyamides, polyimides, or copolymers of these thermoplastics, such as PETG (glycol-modified polyethylene terephthalate).

In other embodiments, the sensors are made using a relatively rigid substrate to, for example, provide structural support against bending or breaking. Examples of rigid materials that may be used as the substrate include glass, poorly conducting ceramics, such as aluminum oxide and silicon dioxide.

The electrodes may be made of any conductive material such as pure metals or alloys, or other conductive materials. Examples include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or metallic compounds of these elements. In certain embodiments, the conductive material includes carbon, gold, platinum, palladium, iridium, or alloys of these metals, since such noble metals and their alloys are unreactive in biological systems. In certain cases, the reference electrode or the reference/counter electrode may be a silver/silver chloride electrode.

Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like.

In certain embodiments, the thickness of spacer layer may be constant throughout, and may be at least about 0.01 mm (10 μm) and no greater than about 1 mm or about 0.5 mm. For example, the thickness may be between about 0.02 mm (20 μm) and about 0.2 mm (200 μm). In one certain embodiment, the thickness is about 0.05 mm (50 μm), and about 0.1 mm (100 μm) in another embodiment.

The sample chamber has a volume sufficient to receive a sample of biological fluid therein. In some embodiments, the sample chamber has a volume that is typically no more than about 1 μL, for example no more than about 0.5 μL, and also for example, no more than about 0.3 μL, 0.25 μL, or 0.1 μL.

The sensing layer may include deposited as an aqueous solution of an analyte specific enzyme and a redox mediator. The sensing layer can be screen-printed, slot coated, deposited using an ink jet, for example. The sensing layer may be disposed in the sample chamber on the working electrode and/or the reference and/or the counter electrode.

A layer of mesh may overlay the electrodes. This layer of mesh may protect the sensing layer from physical damage. The layer of mesh may also facilitate wetting the electrodes by reducing the surface tension of the sample, thereby allowing it to spread evenly over the electrodes. The mesh layer may also facilitate filling of the sample chamber by wicking the sample into the sample chamber. The mesh layer may be made of a polymer.

In certain embodiments, the sensor may not include a mesh layer that ma filter out blood cells, such as, red blood cells. In certain embodiments, the sensor does not include a layer, such as a membrane, that may filter out the blood cells from a sample.

In certain embodiments, the method for measuring a property of a sample does not include applying alternating current (AC) to the electrodes of the sensor. As such, in certain embodiments, a signal measured at an electrode is not an AC signal.

Analyte test strips for use with the invention can be of any kind, size, or shape known to those skilled in the art; for example, FREESTYLE® and FREESTYLE LITE™ test strips, as well as PRECISION™ test strips sold by ABBOTT DIABETES CARE Inc., ACCU-CHEK Aviva test strips, ACCU-CHEK Aviva Plus test strips, CONTOUR® test strips, BREEZE® 2 test strips, OneTouch® test strips, OneTouch® Ultra® test strips. In addition to the embodiments specifically disclosed herein, the reagents and methods of the present disclosure can be configured to work with a wide variety of analyte test strips, e.g., those disclosed in U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. patent application Ser. No. 12/102,374, filed Apr. 14, 2008, and U.S. Patent Application Publication No. 2009/0095625; U.S. Pat. No. 6,616,819; U.S. Pat. No. 6,143,164; U.S. Pat. No. 6,592,745; U.S. Pat. No. 6,071,391 and U.S. Pat. No. 6,893,545; US Patent Application Publication No. US 2007/0272563; U.S. Pat. No. 5,628,890; U.S. Pat. No. 6,764,581; and U.S. Pat. No. 7,311,812, for example, the disclosures of each of which are incorporated by reference herein in their entirety.

Analyte sensors are disclosed in these patent application publication and patents are each herein incorporated by reference in its entirety.

The terms "working electrode", "counter electrode", "reference electrode" and "counter/reference electrode" are used herein to refer to a portion or portions of a conductive trace which are configured to function as a working electrode, counter electrode, reference electrode or a counter/reference electrode respectively. In other words, a working electrode is that portion of a conductive trace which functions as a working electrode as described herein, e.g., that portion of a conductive trace which is exposed to an environment containing the analyte or analytes to be measured and not covered by an insulative layer (such as a spacer layer, a tape, or a cover), and which, in some cases, has been modified with one or more sensing layers as described herein. Similarly, a reference electrode is that portion of a conductive trace which function as a reference electrode as described herein, e.g., that portion of a conductive trace which is exposed to an environment containing the analyte or analytes to be measured and not covered by an insulative layer, and which, in some cases, includes a secondary conductive layer, e.g., a Ag/AgCl layer. A counter electrode is that portion of a conductive trace which is configured to function as a counter electrode as described herein, e.g., that portion of a conductive trace which is exposed to an environment containing the analyte or analytes to be measured and not covered by an insulative layer. As noted above, in some embodiments, a portion of a conductive trace may function as either or both of a counter electrode and a reference electrode.

The dimensions of the analyte sensor may vary. In certain embodiments, the overall length of analyte sensor may be no less than about 10 mm and no greater than about 50 mm. For example, the length may be between about 30 and 45 mm; e.g., about 30 to 40 mm. It is understood, however that shorter and longer sensor strips could be made. In certain embodiments, the overall width of sensor strip may be no less than about 3 mm and no greater than about 15 mm. For example, the width may be between about 4 and 10 mm, about 5 to 8 mm, or about 5 to 6 mm. In one particular example, sensor strip has a length of about 32 mm and a width of about 6 mm. In another particular example, sensor strip has a length of about 40 mm and a width of about 5 mm. In yet another particular example, sensor strip has a length of about 34 mm and a width of about 5 mm.

Representative examples of analyte specific enzymes that may be present in the sample chamber of the analyte sensors in a sensing layer include glucose dehydrogenase, glucose-6-phosphate dehydrogenase, glucose oxidase, cholesterol oxidase, lactate oxidase, β-hydroxybutyrate dehydrogenase, alcohol dehydrogenase, lactate dehydrogenase, formaldehyde dehydrogenase, malate dehydrogenase, and 3-hydroxysteroid dehydrogenase. For example, an enzyme, including a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

Representative examples of redox mediators that may be present in the sample chamber of the analyte sensor, for example, in a sensing layer, include organometallic redox species such as metallocenes including ferrocene or inorganic redox species such as hexacyanoferrate (III), ruthenium hexamine, etc. Additional suitable electron transfer agents usable as redox mediators in the sensors of the present invention are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, including 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(l-vinyl imidazole) (referred to as "PVI") and poly(4-vinyl pyridine) (referred to as "PVP"). Suitable copolymer substituents of poly(l-vinyl imidazole) include acrylonitrile, acrylamide, and substituted or quaternized N-vinyl imidazole, e.g., electron transfer agents with osmium complexed to a polymer or copolymer of poly(l-vinyl imidazole). Embodiments may employ electron transfer agents having a redox potential ranging from about −200 mV to about +200 mV versus the standard calomel electrode (SCE).

Additional examples include those described in U.S. Pat. Nos. 6,736,957, 7,501,053 and 7,754,093, the disclosures of each of which are incorporated herein by reference in their entirety.

Figure 5:
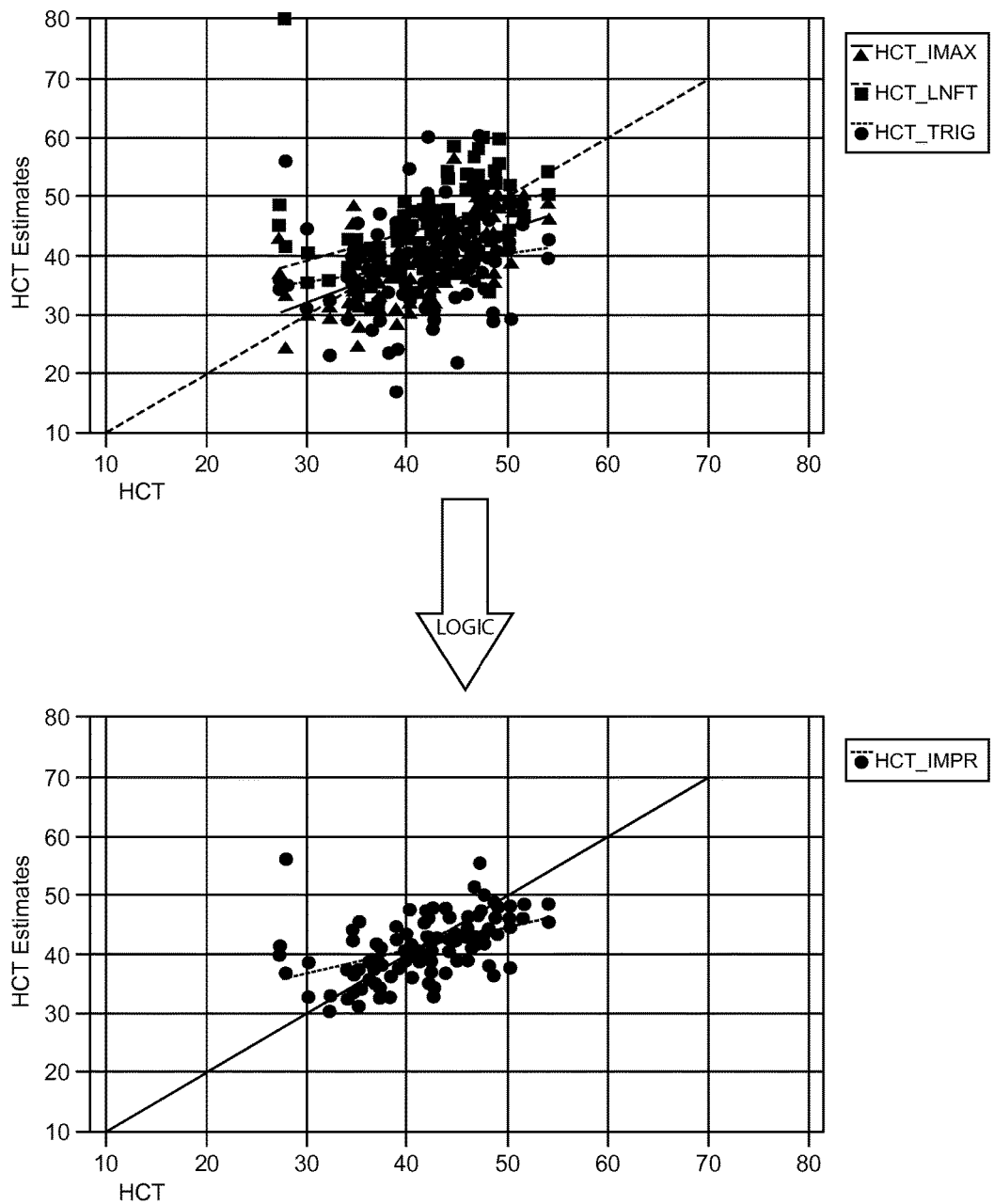
FIG. 5 shows improved hematocrit measurement.

In certain embodiments of the present disclosure, present method results in an improved accuracy of the measurement of a property of a sample than any one measurement alone. For example, making three or more independent measurements of hematocrit, comparing the values obtained by the independent measurements and combining the values that are in agreement while excluding any outliers may result in better correlation between hematocrit as determined by a sensor and a reference hematocrit. FIG. 5 depicts an improved hematocrit measurement obtained by making three independent measurements of hematocrit. In FIG. 5, top panel, hematocrit values measured using interfacial charging current, fill time, and trigger current, as explained herein are depicted. These hematocrit estimates (Y-axis) are plotted against a reference hematocrit X-axis). Application of logic that includes comparing the values obtained by the independent measurements and combining the values that are in agreement while excluding any outliers results in improved hematocrit values that are closer to the reference hematocrit (FIG. 5, bottom panel).

In addition, using the combined hematocrit or concentration of another interferent to correct the concentration of an analyte measured by a sensor may increase the accuracy of the measurement. In certain instances, using the hematocrit or concentration of another interferent measured by the instant method to correct the analyte concentrations as determined by the signal detected from the analyte sensor results in determination of analyte concentration that is within 20% of the reference value, or within 10% of the reference value, or within 5% of the reference value of the reference value.

In some cases, using the hematocrit or concentration of another interferent measured by the instant method to correct the analyte concentration as determined by the signal detected from the analyte sensor results in determination of analyte concentration that is within Zone A of the Clarke Error Grid Analysis. For example, using the hematocrit or concentration of another interferent measured by the instant method to correct the analyte concentrations as determined by the signal detected from the analyte sensor results in determination of analyte concentration that is within Zone A of the Clarke Error Grid Analysis for 75% or more of the analyte sensors, such as 80% or more, or 90% or more, including 95% or more of the analyte sensors. In certain instances, using the hematocrit or concentration of another interferent measured by the instant method to correct the analyte concentrations as determined by the signal detected from the analyte sensor results in determination of analyte concentration that is within Zone A or Zone B of the Clarke Error Grid Analysis. For example, using the hematocrit or concentration of another interferent measured by the instant method to calibrate the analyte concentrations as determined by the signal detected from the analyte sensor results in determination of analyte concentration that is within Zone A or Zone B of the Clarke Error Grid Analysis for 75% or more of the analyte sensors, such as 80% or more, or 90% or more, including 95% or more of the analyte sensors. Further information regarding the Clarke Error Grid Analysis is found in Clarke, W. L. et al. "Evaluating Clinical Accuracy of Systems for Self-Monitoring of Blood Glucose" *Diabetes Care*, vol. 10, no. 5, 1987: 622-628.

Meter and System for Improving Measurement Accuracy

A meter for improving measurement accuracy is also provided. In certain aspects, the meter may include a memory, a processor, and a display. The memory may be operably coupled to the processor, wherein the memory includes instructions stored therein to be executed by the processor.

In certain cases, the instructions may include instructions for obtaining a first measurement of the property of a sample applied to an analyte sensor inserted into the meter; instructions for obtaining a second measurement of the property; instructions for obtaining a third measurement of the property; instructions for deriving a first value, a second value and a third value of the property using the first, second, and third measurements, respectively; instructions for comparing the first, second, and third values to determine whether one of the values is an outlier in comparison with the other two values. In certain cases, when two of the first, second, and third values are in agreement, the instructions may include instructions for providing a single value of the property based on two of the first, second, and third values that are in agreement.

Also disclosed herein is a system for improving measurement accuracy. The system may include a meter as described herein and a sensor. The sensor may be a sensor as described herein, for example, a sensor as depicted in FIG. 1, 2, 6, 7, or 8. In certain cases, the sensor may include a first electrode, a second electrode, and a third electrode. In certain cases, the property may be hematocrit and instructions for obtaining the first measurement includes determining fill-time of the sample by measuring time elapsed between detecting a signal between the first electrode and the second electrode and another signal between the first electrode and the third electrode; instructions for obtaining the second measurement includes measuring a first signal at the second electrode after the sample chamber is substantially filled with the sample; and instructions for obtaining the third measurement includes measuring a second signal at the third electrode.

In certain cases, the sensor may include an enzyme responsive to an analyte and a redox mediator, the meter may further include instructions for measuring an analyte related signal at the second electrode after measuring the first signal and instructions for determining concentration of the analyte using the analyte related signal.

In certain cases, the instructions for determining concentration of the analyte using the analyte related signal may include correcting the analyte related signal using measurement of hematocrit of the sample.

The first and second signals may be as disclosed herein, such as, selected from the group consisting of voltage, current, resistance, capacitance, charge, conductivity, or combination thereof. In certain embodiments, the first and second signals are current. In certain embodiments, the first signal is measured at the second electrode and the second signal is current measured at the third electrode, where the first and second signals are current.

Also disclosed herein is a system that includes a meter and an analyte sensor; the analyte sensor including a sample chamber comprising a first electrode, a second electrode, and a third electrode; an enzyme responsive to the analyte and a redox mediator; the meter including a memory, a processor, and a display, the memory operably coupled to the processor, wherein the memory comprises instructions stored therein to be executed by the processor, the instructions including: instructions for a determining fill-time by measuring time elapsed between detecting a signal between the first electrode and the second electrode and another signal between the first electrode and the third electrode, wherein the fill-time is related to hematocrit of the sample; instructions for measuring a first signal at the second electrode after the sample chamber is substantially filled with the sample, wherein the first signal is substantially independent of the analyte concentration and is related to hematocrit of the sample; instructions for measuring an analyte related signal at the second electrode after measuring the first signal; instructions for measuring a second signal at the third electrode after measuring the analyte related signal, wherein the second signal is related to hematocrit of the sample; instructions for determining concentration of the analyte.

In certain cases, the meter includes instructions for deriving first, second, and third hematocrit values of the sample using the fill-time, the first signal, and the second signal. The meter includes instructions for comparing the first, second, and third hematocrit values of the sample. The meter includes instructions for calculating a single hematocrit value based on the first, second and third hematocrit values when the first, second, and third hematocrit values of the sample are in agreement. The meter includes instructions for calculating a single hematocrit value based on two of the first, second, and third hematocrit values when only the two of the first, second, and third hematocrit values are in agreement. The meter includes instructions for calibrating the concentration of the analyte according to the single hematocrit value.

In certain cases, the meter may display information related to analysis of a sample to user. For example, the meter may display the hematocrit measured, analyte concentration measured, error message, instructions to redo sample analysis by inserting an unused test strip, or the like.

In certain cases, the meter may include an interface for receiving information from a user. In certain cases, the interface may relay the inputted information to the memory, which in turn may use the information in the method for improving measurement accuracy.

Combined Analyte and Hematocrit Sensor

In another aspect, another device and method for determining hematocrit of a sample is provided. The device includes an analyte sensor with separate compartments for measurement of analyte and measurement of viscosity. The analyte sensor comprises a first substrate; a second substrate; a first sample chamber located between the first and second substrates, the first sample chamber comprising a first electrode, a second electrode, and a third electrode; a second sample chamber located between the first and second substrates, the second sample chamber comprising a working electrode and a reference/counter electrode, wherein the first sample chamber is smaller than the second sample chamber.

In certain embodiments, the analyte sensor further comprises a third sample chamber comprising three electrodes, wherein the third sample chamber is bigger than the first sample chamber and smaller than the second sample chamber.

In certain embodiments, the first and second sample chambers are filled from a common opening in the analyte sensor.

In certain embodiments, the first chamber is located downstream of the second chamber or vice versa.

Figure 3:
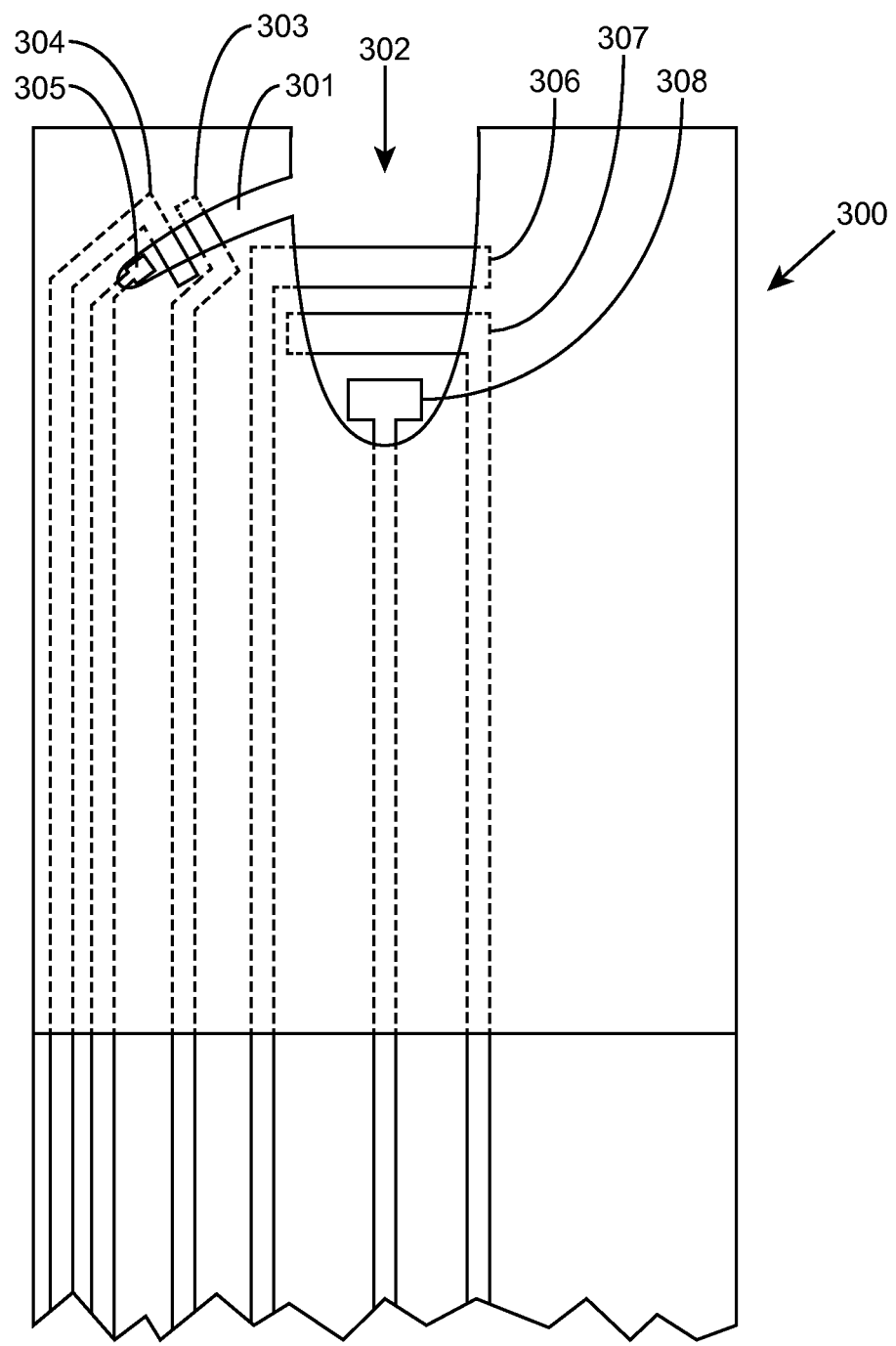
FIG. 3 shows a schematic of an exemplary analyte sensor.

In addition, the present disclosure includes a method of using the analyte sensor comprising separate compartments for measurement of analyte and measurement of viscosity. In certain embodiments, the method comprises contacting a sample with the analyte sensor 300 (FIG. 3), the analyte sensor comprising a first substrate; a second substrate; a first sample located between the first and second substrates, the first sample chamber comprising a first electrode 303, a second electrode 304, and a third electrode 305; a second sample chamber 302 located between the first and second substrates, the second sample chamber comprising a working electrode 307 and a reference/counter electrode 306 and an trigger electrode 308, wherein the first sample chamber 301 is smaller than the second sample chamber 302; detecting a first signal between the first electrode and the second electrode to determine that the first sample chamber is beginning to fill with the sample; detecting a second signal between the first electrode or the second electrode) and the third electrode to determine that the first sample chamber is substantially filled with the sample; determining time elapsed between detecting the first and second signals; correlating the time to a property of the sample.

In certain cases, the property of the sample is hematocrit and the time required to fill ("fill time") the first sample chamber is directly correlated to hematocrit of the sample. In certain embodiments, the method further includes using the fill time to determine the hematocrit of the sample.

In certain cases, the sensor used in the method further comprises a third sample chamber comprising three electrodes, wherein the third sample chamber is bigger than the first sample chamber and smaller than the second sample chamber and the method comprises determining the fill time of the third sample chamber and determining hematocrit of the sample.

Method for Determining Hematocrit

Hematocrit can vary between individuals. Hematocrit is normally about 45% for men and 40% for women. Hematocrit may be about 20% for individuals with anemia or 60% in newborns. In general, a one percent variation in hematocrit may result in about a one percent variation in glucose concentration determination. The methods described herein reduce the variation in the glucose or other analyte concentration, measured using an analyte sensor, due to differences in hematocrit. In certain cases, the variation is reduced by calibrating, such as, correcting the analyte concentration by using the hematocrit of the sample.

In certain embodiments, the fill-time may be used to determine the hematocrit of the sample by correlating the fill-time to known hematocrit values at a reference temperature. For example, a device connected to the sensor or the measuring device (e.g., meter) may be programmed to calculate hematocrit values from the fill times at a particular temperature. In certain embodiments, an algorithm may be used to calculate the hematocrit based on the fill time and the ambient temperature. Hematocrit and temperature affects the viscosity of a sample. The higher the hematocrit, more viscous the sample, and longer the fill-time, while the higher the temperature, less viscous the sample and shorter the fill-time. In certain embodiments, the peak interfacial charging current ($I_c$) measured at the working electrode may be used to determine the hematocrit of the sample by correlating the current to known hematocrit values. The peak interfacial charging current is dependent on the resistance of the sample, which resistance depends upon the hematocrit of the sample. In general, higher the hematocrit of the sample, higher the resistance of the sample, and lower the $I_c$. A device connected to the sensor or the measuring device (e.g., meter) may store hematocrit values of several samples (as measured by an accurate device) and $I_c$ of the samples, thus providing a relationship of $I_c$ to hematocrit value. In certain embodiments, an algorithm may be used to calculate the hematocrit based on the peak interfacial charging current and the ambient temperature.

Similarly, the trigger current ($I_t$) may be used to determine the hematocrit of a sample by correlating $I_t$ to hematocrit values from samples with known $I_t$. In general, higher the hematocrit of the sample, higher the resistance of the sample, and lower the $I_t$. In certain cases, the trigger current may be an integrated current from current obtained over a certain time period, for example, a period of about 3 sec, or 2 sec, or 1 sec, or 0.5 sec, or 0.2 sec, or less. In certain embodiments, an algorithm may be used to calculate the hematocrit based on the trigger current and the ambient temperature.

In certain cases, the method of determining hematocrit may include measuring analyte related signal, for example, glucose related signal, at two different time points after contacting the sample with test strip. A first analyte concentration determination as measured at a first time differs from a second analyte concentration measured at a second time based on hematocrit due to a difference in sensitivity to hematocrit at the two different measurement times. The difference in the first and second analyte related signals may be used to calculate the hematocrit. Therefore, a fourth measurement of hematocrit of a sample may be obtained and used to determine a single, more accurate level of hematocrit by using the four independently measured hematocrit values.

In certain cases, the method further comprises displaying the hematocrit to a user. The hematocrit value may be displayed or an indication of hematocrit is normal, high, or low may be displayed. The display may be on the meter in which the sensor is inserted or on another display device connected to the meter, such as, a computer, or smart phone.

In certain embodiments, the reader for the analyte sensor may include programming to determine a property of the sample, such as, hematocrit. In certain cases, the reader, e.g., meter may include a user interface allowing the user to input additional information, such as, gender and/or age of the user; any medication or medical procedure the user may be using, such as, acetaminophen, or dialysis; medical condition, such as, anemia. One or more of user specific information may be used in the method for improving measurement accuracy of an analyte in a sample from the user.

Method of Calculating Analyte Concentration with Compensation for Hematocrit

The hematocrit value of a sample may be used to adjust the analyte concentration measured by an analyte sensor. In general, hematocrit is inversely related to response of a sensor to an analyte. In general, a higher hematocrit results in a lower analyte-specific response from the sensor and measurement of a lower concentration and vice versa.

As such, the analyte concentration may be adjusted by multiplying with a factor to generate a final concentration or a hematocrit compensated concentration. For example, if the hematocrit is determined to be lower than a hematocrit range or a hematocrit value then the analyte concentration may be decreased by a certain percentage. If the hematocrit is determined to be higher than a hematocrit range or a hematocrit value then the glucose concentration may be increased by a certain percentage. For example, for every percent increase in hematocrit compared to a normal hematocrit, the analyte concentration may be increased by a factor and for every percent decrease in hematocrit compared to a normal hematocrit, the analyte concentration may be decreased by a factor. The factor may be a correction factor that may be predetermined. For example, a predetermined correction factor may be stored in a measurement device that calculates the analyte concentration. In certain cases, the measurement device may be a meter.

In certain embodiments, the hematocrit range to which a hematocrit measured as described herein is compared to a reference range from about 37% to about 47%. In certain embodiments, the hematocrit measured as described herein is compared to an reference hematocrit value of about 37%, or 40%, or 47%, for example 42%.

In certain cases, if hematocrit is low or high compared to a reference, such as, a reference range or reference value, the method further comprises applying an algorithm to adjust a measurement of analyte concentration based on the measured hematocrit.

In certain cases, if the hematocrit is close to about 42% hematocrit then no correction of analyte concentration is performed.

In certain embodiments, for every percent increase or decrease in hematocrit compared to a reference range of 37% to 47%, such as, a reference value of 37%, 40%, 42%, 43%, 44%, or 45%, the concentration of the analyte is decreased or increased, respectively, by a correction factor.

Measurement of Surface Electrochemical Reaction to Determine Hematocrit

In another aspect, a method for determining hematocrit of a whole blood sample is provided. The method comprises contacting an analyte sensor comprising a working electrode and a counter/reference electrode with the whole blood sample, wherein the working electrode comprises an electrochemically active compound and the whole blood sample comprises a reactant that reacts with the electrochemically active compound, wherein the electrochemically active compound reacts at a different potential than an analyte present in the whole blood sample; measuring a signal generated at the working electrode, wherein the signal is inversely related to the hematocrit of the whole blood sample; correlating the signal to determine hematocrit of the whole blood sample. The hematocrit may then be used to recalculate the analyte concentration.

In certain embodiments, the electrochemically active compound is silver and the reactant is chloride ion. In certain embodiments, the potential applied for reacting silver with chloride ion is 300 mV and the analyte is glucose and the potential applied for measuring glucose concentration is 200 mV.

Application of the Analyte Sensor

The property of a sample, such as, concentration of an analyte as measured using an analyte sensor may be calculated by amperometry, coulometry, potentiometry, and/or voltametry, including square wave voltammetry.

A common use for methods of the present invention is for the determination of a property of a biological fluid, such as blood, interstitial fluid, and the like, in a patient or other user. As noted earlier, the property of a sample may be concentration of an analyte. Analytes that may be determined include but are not limited to, for example, glucose, acetyl choline, amylase, bilirubin, cholesterol, chorionic gonadotropin, glycosylated hemoglobin (HbAlc), creatine kinase (e.g., CK-MB), creatine, DNA, fructosamine, glucose, glutamine, growth hormones, hormones, ketones, ketone bodies, lactate, peroxide, prostate-specific antigen, prothrombin, RNA, thyroid stimulating hormone, and troponin. In certain cases, the analyte sensor determines the concentration of glucose. In certain cases, the analyte sensor may determine concentration of ketone or ketone bodies.

Multiple analyte sensors as disclosed herein may be packaged together and sold as a single unit; e.g., a package of about 25, about 50, or about 100 sensors, or any other suitable number. A kit may include one or more sensors, and additional components such as control solutions and/or lancing device and/or meter, etc.

The analyte sensor may be used to provide the concentration of an analyte present in a body fluid sample by using a coulometric technique, a potentiometric technique or an amperometric technique. In certain embodiments, the sensor is connected to an amperometer to detect and provide concentration of an analyte, e.g., glucose. Sensors are generally configured for use with an electrical meter, which may be connectable to various electronics. As mentioned above, the meter may be a coulometer, a potentiometer or an amperometer. A meter may be available at generally the same locations as the sensors, and sometimes may be packaged together with the sensors, e.g., as a kit.

In certain cases, the meter or another measurement device connected to the analyte sensor may be used to perform the methods described herein. In certain embodiments, the meter or measurement device, such as, hand-held reader, e.g., a reader module connectable to a personal device, such as, a smart phone, may comprise programming to carry out the above described methods. In certain cases, the meter may be programmed to use an algorithm to compare a plurality of measurements of a property to detect whether an outlier value is present.

Examples of suitable electronics connectable to the meter include a data processing terminal, such as a personal computer (PC), a portable computer such as a laptop or a handheld device (e.g., personal digital assistants (PDAs)), and the like. The electronics are configured for data communication with the receiver via a wired or a wireless connection. Additionally, the electronics may further be connected to a data network (not shown) for storing, retrieving and updating data corresponding to the detected analyte level (e.g., glucose level) of the user.

The various devices connected to the meter may wirelessly communicate with a server device, e.g., using a common standard such as 802.11 or Bluetooth RF protocol, or an IrDA infrared protocol. The server device could be another portable device, such as a Personal Digital Assistant (PDA) or notebook computer, or a larger device such as a desktop computer, appliance, etc. In some embodiments, the server device has a display, such as a liquid crystal display (LCD), as well as an input device, such as buttons, a keyboard, mouse or touch-screen. With such an arrangement, the user can control the meter indirectly by interacting with the user interface(s) of the server device, which in turn interacts with the meter across a wireless link.

The server device may also communicate with another device, such as for sending data from the meter and/or the service device to a data storage or computer. For example, the service device could send and/or receive instructions (e.g., an insulin pump protocol) from a health care provider computer. Examples of such communications include a PDA synching data with a personal computer (PC), a mobile phone communicating over a cellular network with a computer at the other end, or a household appliance communicating with a computer system at a physician's office.

A lancing device or other mechanism to obtain a sample of biological fluid, e.g., blood, from the patient or user may also be available at generally the same locations as the sensors and the meter, and sometimes may be packaged together with the sensor and/or meter, e.g., as a kit.

The sensors are particularly suited for inclusion in an integrated device, i.e., a device which has the sensor and a second element, such as a meter or a lancing device, in the device. The integrated device may be based on providing an electrochemical assay or a photometric assay. In some embodiments, sensors may be integrated with both a meter and a lancing device. Having multiple elements together in one device reduces the number of devices needed to obtain an analyte level and facilitates the sampling process. For example, embodiments may include a housing that includes one or more of the sensor strips, a skin piercing element and a processor for determining the concentration of an analyte in a sample applied to the strip. A plurality of sensors may be retained in a cassette in the housing interior and, upon actuation by a user, a single sensor may be dispensed from the cassette so that at least a portion extends out of the housing for use.

Operation of the Analyte Sensor

In use, a sample, such as a sample of biological fluid is provided into the sample chamber of a sensor, where a property of the sample is determined. The analysis may be based on providing an electrochemical assay or a photometric assay. In many embodiments, it is the hematocrit and the concentration of glucose in blood that is determined. Also in many embodiments, the source of the biological fluid is a drop of blood drawn from a patient, e.g., after piercing the patient's skin with a lancing device, which could be present in an integrated device, together with the sensor strip.

Prior to providing the sample to the sensor, or even after providing the sample to the sensor, there may be no need for the user to input a calibration code or other information regarding the operation and/or interaction of the sensor with the meter or other equipment. The sensor may be configured so that the results received from the analysis are clinically accurate, without the user having to adjust the sensor or the meter. The sensor is physically configured to provide accurate results that are repeatable by a batch of sensors.

After receipt of the sample in the sensor, the analyte in the sample is, e.g., electrooxidized or electroreduced, at the working electrode, where the level of current obtained is proportional to analyte concentration. The sensor may be operated with or without applying a potential to the working electrode. In one embodiment, the electrochemical reaction occurs spontaneously and a potential need not be applied between the working electrode and the counter electrode. In another embodiment, a potential is applied between the working electrode and the counter electrode.

Manufacturing of Analyte Sensor

Analyte sensor or sensor strips discussed above, are sandwiched or layered constructions having first and second substrates spaced apart by a spacer layer and optionally including a mesh layer in the sample chamber defined by the first and second substrates and the spacer layer. Such a construction can be made by combining the various layers together in any suitable manner. An alternate method for making sensor strips as described herein is to mold the sensors.

In general, the method of manufacturing sensor strips involves positioning a working electrode and a reference and/or a counter electrode on the first or the second substrates, contacting at least a portion of the working electrode and/or reference and/or counter electrode with a sensing layer composition.

Optionally, providing a mesh in the sample chamber defined by the first and second substrates and the spacer layer.

Other embodiments and modifications within the scope of the present disclosure will be apparent to those skilled in the relevant art. Various modifications, processes, as well as numerous structures to which the embodiments of the invention may be applicable will be readily apparent to those of skill in the art to which the invention is directed upon review of the specification. Various aspects and features of the invention may have been explained or described in relation to understandings, beliefs, theories, underlying assumptions, and/or working or prophetic examples, although it will be understood that the invention is not bound to any particular understanding, belief, theory, underlying assumption, and/or working or prophetic example. Although various aspects and features of the invention may have been described largely with respect to applications, or more specifically, medical applications, involving diabetic humans, it will be understood that such aspects and features also relate to any of a variety of applications involving non-diabetic humans and any and all other animals. Further, although various aspects and features of the invention may have been described largely with respect to applications involving in vitro disposable single use sensor strips, it will be understood that such aspects and features also relate to any of a variety of sensors that are suitable for use in connection with the body of an animal or a human, such as those suitable for use as partially implanted sensors, such as transcutaneous or subcutaneous sensors or fully implanted in the body of an animal or a human. Finally, although the various aspects and features of the invention have been described with respect to various embodiments and specific examples herein, all of which may be made or carried out conventionally, it will be understood that the invention is entitled to protection within the full scope of the appended claims.

The following examples are put forth so as to provide those of ordinary skill in the art with a complete disclosure and description of how to make and use the embodiments of the invention, and are not intended to limit the scope of what the inventor regards as the invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Hematocrit Compensation in an Analyte Sensor with Coplanar Electrodes

Glucose sensors were used to measure glucose related signal, fill-time of sample chamber and two glucose unrelated signals, each of the fill-time and the glucose unrelated signals were sensitive to sample hematocrit.

Figure 2:
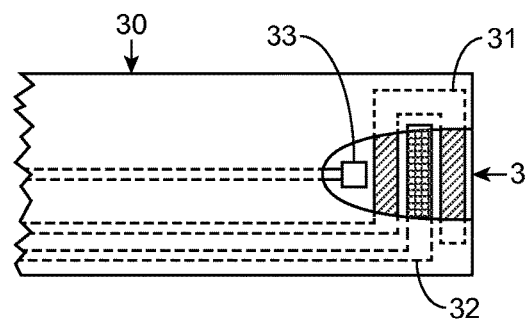
FIG. 2 illustrates the configuration of the electrodes in an analyte sensor.

FIG. 2 shows the configuration of the electrodes in the glucose sensor 30. The sensor included a dual purpose counter/reference electrode 31, a working electrode 32, and a trigger electrode 33. Each of the electrodes had a well-defined area that was maintained across the different sensors used in the experiment.

Glucose sensor was inserted into a meter. A sample was applied to the glucose sensor at the sample application site 3. A first potential was applied between the reference/counter electrode and the working electrode and a second potential was applied between the reference/counter electrode and the trigger electrode. A first current was measured at the working electrode to determine when the sample was beginning to fill the sample chamber. After measuring the first current, a second current was measured at the trigger electrode to determine when the sample chamber was substantially filled with the sample. The time difference between the detection of the first and second currents was used to determine the fill-time. This fill-time is related to the hematocrit of the sample.

After the sample chamber was determined to be substantially filled, working and trigger electrodes were briefly disconnected and then reconnected to the reference/counter electrode (via the meter). A potential was applied between the reference/counter electrode and the working electrode and another potential was applied between the reference/counter electrode and the trigger/trigger electrode.

Figure 4:
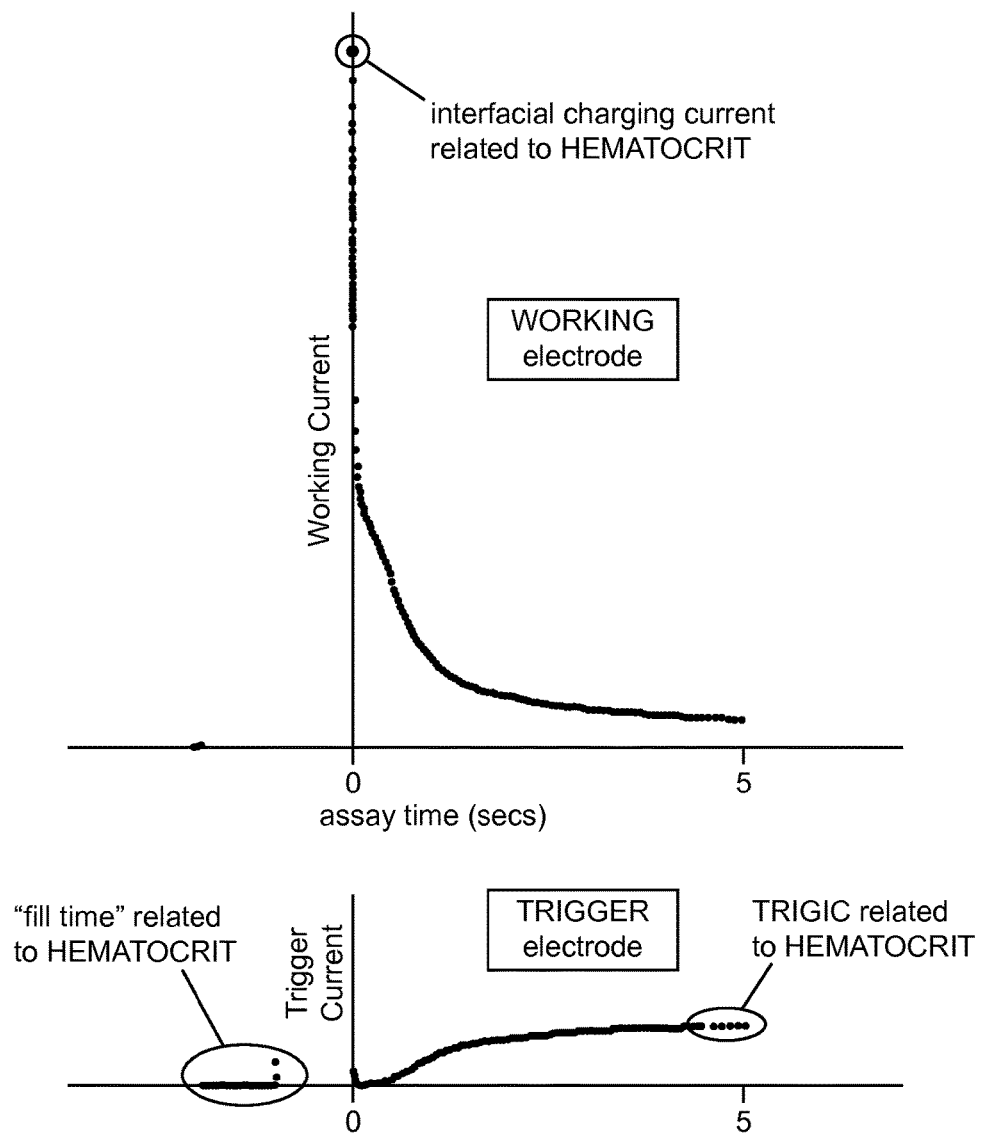
FIG. 4 shows the currents measured at the working electrode and the trigger electrode.

FIG. 4 shows the currents measured at the working electrode (top panel) and the trigger electrode (bottom panel). An interfacial charging current at the working electrode was measured immediately after application of potential, with a high sampling frequency. This interfacial charging current is related to the hematocrit of the sample. A trigger current related to hematocrit was obtained from the trigger electrode. The trigger integrated current (TRIGIC) is derived from an integration of the current measured at the trigger electrode at the indicated assay time. The assay time plotted on the X-axis refers the time points at which interfacial charging current and trigger current are measured after detection of substantial filling of the sample chamber by the sample.

Glucose related current was also measured at the working electrode. The application of potential to the working electrode was then discontinued and current at the trigger electrode was measured.

Each of the fill-time, interfacial charging current, and trigger current were used to independently determine hematocrit of the sample.

FIG. 5 shows improved hematocrit measurement through signal combination logic-controlled averaging of hematocrit values determined by the fill-time, interfacial charging current, and trigger current. The logic was used to identify and eliminate any hematocrit value that was an outlier when compared to the other two hematocrit values. FIG. 5, the first graph (Top Panel) shows a plot of hematocrit measured based on maximum interfacial charging current (HCT_IMAX; triangles), fill time (HCT_LNFT; squares), and trigger current (HCT_TRIG; circles). FIG. 5, the second graph (Bottom Panel) shows the hematocrit values (HCT_IMPR) obtained by applying the signal combination logic to the individual hematocrit values (HCT-IMAX, HCT-LNFT and HCT-TRGIC). The logic employed is explained in the detailed description section. Abbreviations used for FIGS. 4 and 5: "secs"—seconds; "TRIGIC"—trigger integrated current; "HCT_IMAX"—Hematocrit_Peak Interfacial Charging Current; "HCT_LNFT"—Hematocrit_natural log of fill time; "HCT_TRIG"—Hematocrit_Trigger Integrated Current; "HCT-IMPR"—Hematocrit_Improved.

EXAMPLE 2

Figure 6:
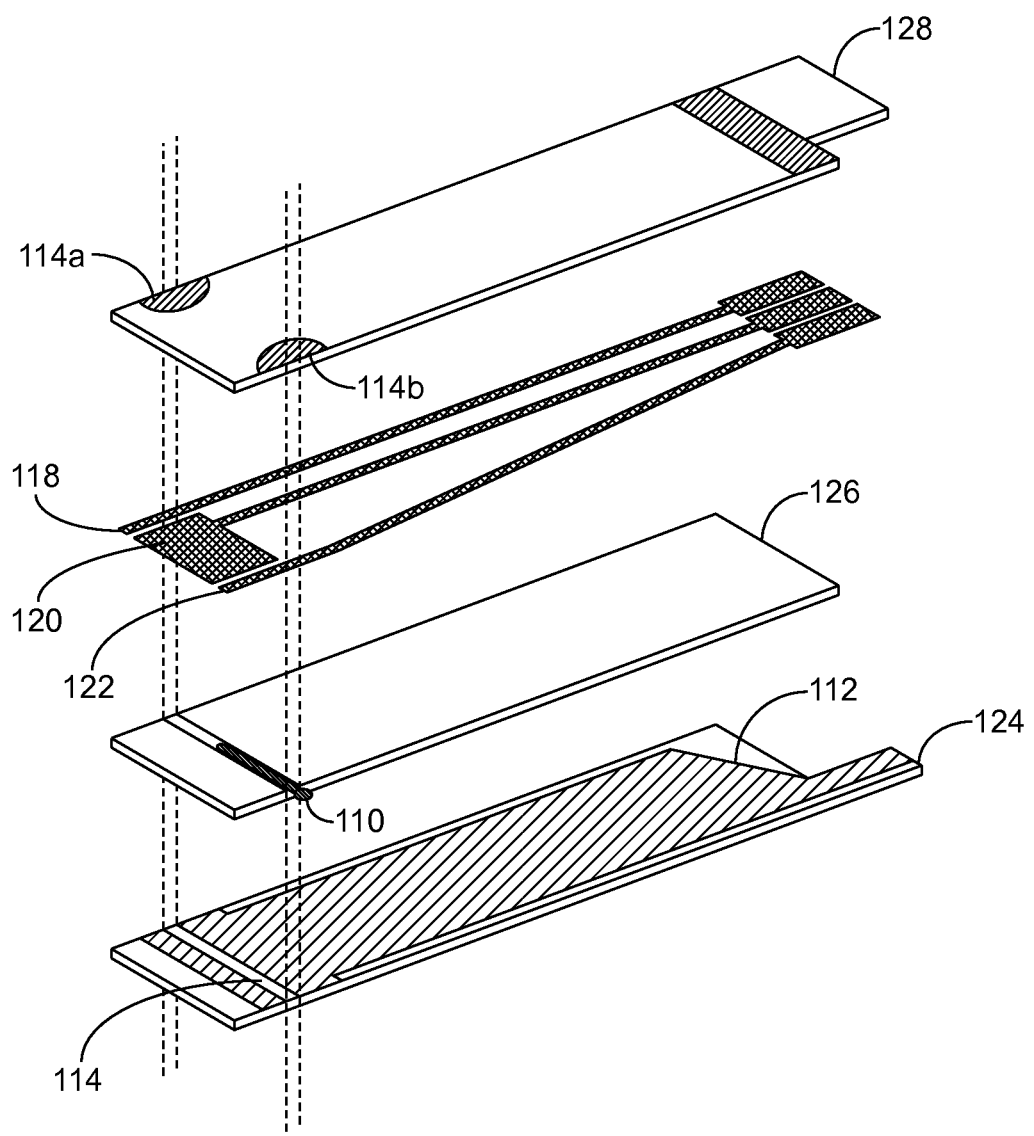
FIG. 6 shows an embodiment of an analyte sensor for use in the methods disclosed herein.
Figure 8:
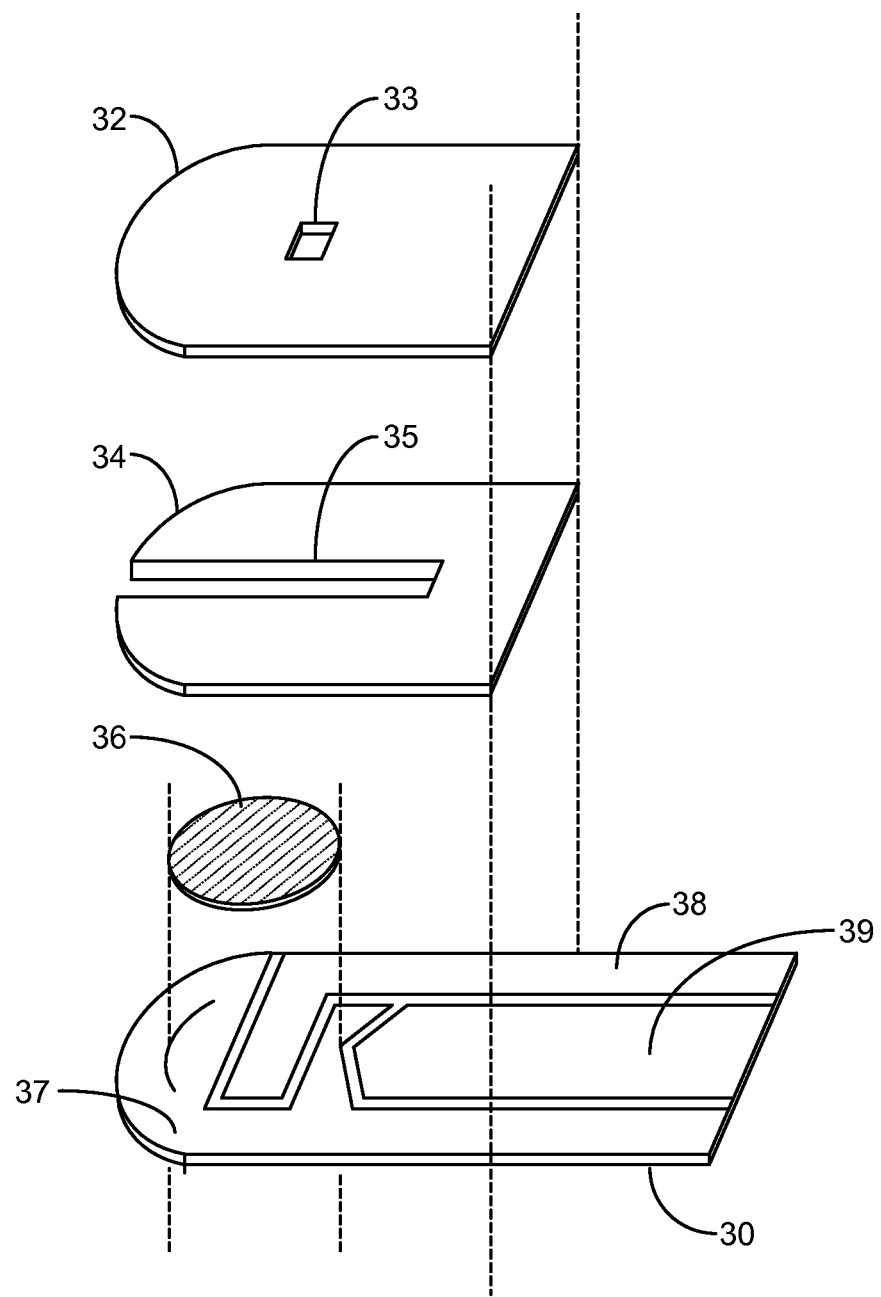
FIG. 8 shows an embodiment of an analyte sensor for use in the methods disclosed herein.

Hematocrit Compensation in an Analyte Sensor with Facing Electrode Configuration An analyte sensor with electrodes in a facing configuration is used to provide at least three measurements of hematocrit of a sample applied to the sensor. An exploded view of such a sensor is shown in FIG. 6. The sensor includes a working electrode 112 disposed on substrate 124. Electrodes 118, 120, and 122 are disposed on second substrate 128. Spacer layer 126 (an adhesive) separates working electrode 112 from electrodes 118, 120, and 122. 118 and 122 are trigger electrodes and 120 is a silver/silver chloride combined counter/reference electrode. Substrates 128, 124, in combination with spacer 126 define the sample chamber 114. Sample chamber 114 includes two entrances on side edges of the sensor, the entrance are marked by marking 114a and 114b. 110 depicts a sample as it is filled into the sample chamber 114. Sample chamber 114 includes the working electrode 112. The trigger electrode closest to the side where the sample has been applied indicates when the sample has started filling the sample chamber and the trigger electrode at the opposite side of the sample chamber indicates when the sample chamber has been filled by the sample.

The sensor 108 is inserted into an analyte sensor reader and a sample 110 is applied to the sensor. The reader monitors a current between electrodes 122 and 112 and between electrodes 118 and 112 to determine which side the sample is applied and when the sample is beginning to fill the sample chamber of 114. If the reader detects a current between electrodes 122 and 112, it determines that the sample was applied at 114b. The reader monitors the current between electrodes 112 and 118, detection of a current between 118 and 112 indicates that the sample has filled the sample chamber. The time elapsed between measurement of the two currents is the fill-time for the sample, which is directly proportional to the hematocrit of the sample.

The reader then measures a charging current at the working electrode 112 with a high sampling frequency to obtain a peak charging current. This peak charging current is related to the hematocrit of the sample.

The reader also measures the current at electrodes 122 and/or 118 to obtain a third signal related to hematocrit of the sample.

The reader also measures a signal at the working electrode 112 which is related to the electrolysis of the analyte in the sample and determines a concentration of the analyte.

The reader derives hematocrit values based on fill time, charging current and current at electrodes 122 and/or 118. The reader compares the hematocrit values to determine whether there is an outlier. If no outlier is found, the reader calculates a single hematocrit value from the hematocrit values. If a single outlier is identified, the reader calculates a single hematocrit value from the hematocrit values that are in agreement. If none of the values are in agreement, then a single hematocrit value is not calculated.

When a single hematocrit value is calculated, the reader adjusts the measured analyte concentration using the hematocrit value.

EXAMPLE 3

Hematocrit Compensation in an Analyte Sensor with Facing Electrode Configuration An analyte sensor with electrodes in a facing configuration but with only three electrodes is used to provide at least three measurements of hematocrit of a sample applied to the sensor. The sensor 62 is shown FIGS. 7A-7C. The sensor includes a first substrate 79 with two electrodes 76 and 76' disposed on the substrate; a second substrate 78 with another electrode 63 disposed on it. A spacer layer 60 separates the electrodes 76 and 76' from electrode 63. At the proximal end of the sensor, a sample chamber 61, defined by the two substrates and spacer 60, is located. The sample chamber includes two entrances (70) at opposite side edges of the sensor. At the distal end of the sensor, the substrate 79 includes a notch 90 that exposes the distal end of electrode 63, allowing it to connect to an analyte sensor reader. Substrate 78 is shorter than substrate 79, exposing distal ends of electrodes 76 and 76' for connection to an analyte sensor reader. A sensing layer 72 is included in the sample chamber.

After the sensor 62 is inserted into a meter, the meter monitors the current between electrodes 76 and 63 and between 76' and 63. If the sample is filled from the entrance closer to electrode 76 than 76', the meter detects a current between electrodes 76 and 63. The meter continues to monitor the current between electrodes 76' and 63. When the meter detects current between electrodes 76' and 63, the sample has filled the sample chamber. The meter determines the fill-time for the sample by calculating the time elapsed between detection of current between electrodes 76 and 63 and detection of current between electrodes 76' and 63. The meter also determines the peak charging current at electrode 63. In addition, the meter measures the current at electrodes 76 or 76'. In addition the meter measures an analyte related signal.

The meter derives three hematocrit values based on fill time, charging current and current at electrodes 76 or 76'. The meter compares the three hematocrit values to determine whether there is an outlier. If no outlier is found, the meter calculates a single hematocrit value from the three values. If a single outlier is identified, the meter calculates a single hematocrit value from the two values that are in agreement. If none of the values are in agreement, then a single hematocrit value is not calculated.

When a single hematocrit value is calculated, the meter adjusts the measured analyte concentration using the hematocrit value.

When none of the three hematocrit values are in agreement, the meter outputs the analyte concentration without adjusting the concentration.

EXAMPLE 4

Hematocrit Compensation in an Analyte Sensor with Coplanar Electrode Configuration An analyte sensor with electrodes in a coplanar configuration is used to provide at least three measurements of hematocrit of a sample applied to the sensor. An exploded view of the sensor is shown FIG. 8. Three electrodes 37, 38, and 39 are present on a lower substrate 30. Electrode 39 is the trigger electrode, electrode 37 is reference/counter electrode, and electrode 38 is working electrode. An analyte sensing layer 36 is disposed on electrodes 37 and 38. A spacer layer 34 with a cut out 35 provides a path for the sample. The upper substrate 32 includes an opening 33 to vent air as a sample fills the sample chamber defined by the upper and lower substrates and spacer layer.

The sensor is inserted into a meter comprising programming for measuring at least three signals related to hematocrit of a sample. Insertion of the sensor wakes up the meter which starts to monitor a signal between electrodes 37 and 38. When the meter detects a current between electrodes 37 and 38, it monitors a signal between either electrodes 37 and 39 or between electrodes 38 and 39. When the meter detects a current between electrodes 37 and 39 or between electrodes 38 and 39, it determines that the sample chamber has been filled. The meter calculates the fill time by determining the time elapsed between detecting current between electrodes 37 and 38 ($t_1$) and detecting current between electrodes 38 and 39 ($t_2$) or between 37 and 39 ($t_2$).

The meter further determines the peak charging current at electrode 38. In addition, the meter measures the current at electrode 39. In addition the meter measures an analyte related signal at electrode 38.

The meter derives three hematocrit values based on fill time, charging current and current at electrode 39. The meter compares the three hematocrit values to determine whether there is an outlier. If no outlier is found, the meter calculates a single hematocrit value from the three values. If a single outlier is identified, the meter calculates a single hematocrit value from the two values that are in agreement. If none of the values are in agreement, then a single hematocrit value is not calculated.

When a single hematocrit value is calculated, the meter adjusts the measured analyte concentration using the hematocrit value.

When none of the three hematocrit values are in agreement, the meter outputs the analyte concentration without adjusting the concentration.

The invention claimed is:

1. A meter for measuring hematocrit of a sample, the meter configured for insertion of a sensor comprising a sample chamber comprising a first electrode, a second electrode, and a third electrode, and comprising:
   a memory comprising instructions stored therein and coupled to a processor for executing the instructions stored in the memory of the meter, wherein the instructions, when executed, cause the processor to:
   determine fill-time by measuring time elapsed between detecting a signal between the first electrode and the second electrode and another signal between the first electrode and the third electrode, wherein the fill-time is related to hematocrit of the sample;
   measure a first signal at the second electrode after the sample chamber is filled with the sample, wherein the first signal is independent of the analyte concentration and is related to hematocrit of the sample;
   measure a second signal at the third electrode, wherein the second signal is related to hematocrit of the sample;
   derive, by using the processor executing instructions stored in the memory, a first hematocrit value, a second hematocrit value and a third hematocrit value of the property using the full-time, the first signal, and the second signal, respectively;
   compare the first, second, and third hematocrit values to determine whether one of the values is an outlier; and
   calculate a single hematocrit value of the property based on at least two of the first, second, and third hematocrit values that are in agreement.

2. The meter of claim 1, wherein when the first, second, and third hematocrit values are in agreement, and wherein the single hematocrit value is calculated from the first, second, and third hematocrit values.

3. The meter of claim 1, wherein the sensor comprises an enzyme responsive to an analyte and a redox mediator, and wherein the instructions, when executed, cause the processor to: measure an analyte related signal at the second electrode after determining the fill-time is determined; determine the concentration of the analyte using the analyte related signal; and correcting the concentration of the analyte.

4. The meter of claim 1, wherein the first and second signals are selected from voltage, current, resistance, capacitance, charge, conductivity, or a combination thereof.

5. A system for determining concentration of an analyte in a sample, the system comprising an analyte measurement instrument and an analyte sensor, the analyte sensor comprising a sample chamber comprising a first electrode, a second electrode, and a third electrode; an enzyme responsive to the analyte and a redox mediator;

the analyte measurement instrument comprising a memory comprising instructions stored therein and coupled to a processor for executing instructions stored in the memory of the instrument, wherein the instructions, when executed, cause the processor to:

determine fill-time by measuring time elapsed between detecting a signal between the first electrode and the second electrode and another signal between the first electrode and the third electrode, wherein the fill-time is related to hematocrit of the sample;

measure a first signal at the second electrode after the sample chamber is filled with the sample, wherein the first signal is independent of the analyte concentration and is related to hematocrit of the sample;

measure an analyte related signal at the second electrode after measuring the first signal;

measure a second signal at the third electrode after measuring the analyte related signal, wherein the second signal is related to hematocrit of the sample;

derive first, second, and third hematocrit values of the sample using the fill-time, the first signal, and the second signal;

compare the first, second, and third hematocrit values of the sample;

calculate a single hematocrit value based on at least two of the first, second and third hematocrit values when the at least two of the first, second, and third hematocrit values are in agreement;

determine concentration of the analyte; and correct the concentration of the analyte according to the single hematocrit value.

6. The system of claim 5, wherein the single hematocrit value is calculated based on the first, second and third hematocrit values when the first, second, and third hematocrit values of the sample are in agreement.

7. The system of claim 5, wherein the first and second signals are selected from voltage, current, resistance, impedance, capacitance, or a combination thereof.

8. The system of claim 5, wherein the analyte is glucose.

9. The system of claim 8, wherein the enzyme comprises glucose dehydrogenase or glucose oxidase.

10. The system of claim 9, wherein the glucose dehydrogenase is nicotinamide dinucleotide glucose dehydrogenase (NAD-GDH), pyrrole quinoline quinone glucose dehydrogenase (PQQ-GDH), or flavin-adenine dinucleotide glucose dehydrogenase (FAD-GDH).

11. The system of claim 5, wherein the analyte is β-hyroxybutyrate.

12. The system of claim 11, wherein the enzyme is hydroxybutyrate dehydrogenase.

13. The system of claim 5, wherein the first, second, and third electrodes are coplanar.

14. The system of claim 5, wherein one of the first, second, and third electrodes is in facing configuration with the other two electrodes.

15. The system of claim 5, wherein the electrodes are arranged such that the sample contacts the first electrode before contacting the third electrode.

16. The system of claim 5, wherein the electrodes are arranged such that the sample contacts the second electrode before contacting the third electrode.

17. A system for determining analyte concentration of a sample, the system comprising an analyte sensor and a meter, the analyte sensor comprising a sample chamber comprising a reference/counter electrode, a working electrode, a trigger electrode, an enzyme responsive to the analyte, and a redox mediator;

the meter comprising a processor for executing instructions stored in a memory of the meter, wherein the memory comprising instructions stored therein is coupled to the processor, wherein the instructions, when executed, cause the processor to:

determine fill-time by measuring time elapsed between detecting a signal between the reference/counter electrode and the working electrode and another signal between the reference/counter electrode and the trigger electrode, wherein the fill-time is related to hematocrit of the sample;

disconnect the reference/counter electrode from the working electrode and from the trigger electrode after the sample chamber is substantially filled with the sample;

reconnect the reference/counter electrode to the working electrode and the trigger electrode;

measure a first signal at the working electrode, wherein the first signal is independent of the analyte concentration and is related to hematocrit of the sample;

measure an analyte related signal at the working electrode after measuring the first signal;

measure a second signal at the trigger electrode after measuring the analyte related signal, wherein the second signal is related to hematocrit of the sample;

derive first, second, and third hematocrit values of the sample using the fill-time, the first signal, and the second signal;

compare the first, second, and third hematocrit values of the sample;

calculate a single hematocrit value based on at least two of the first, second and third hematocrit values when the at least two of the first, second, and third hematocrit values are in agreement;

determine concentration of the analyte; and correct the concentration of the analyte according to the single hematocrit value.

18. The meter of claim 17, wherein the first and second signals are current, voltage, resistance, impedance, capacitance, or a combination thereof.

19. The meter of claim 17, wherein the first signal is peak interfacial charging current.

20. The meter of claim 19, wherein the second signal is integrated current.

21. The meter of claim 17, wherein the analyte is glucose.

22. The meter of claim 17, wherein the reference/counter electrode, the working electrode and the trigger electrode are coplanar.

* * * * *